United States Patent
Miyata

(10) Patent No.: US 6,680,370 B1
(45) Date of Patent: Jan. 20, 2004

(54) MEG-4 PROTEIN

(75) Inventor: Toshio Miyata, 102 Ekuseru Isehara, 16-25, Sakuradai 2-chome, Isehara-shi, Kanagawa 259-1132 (JP)

(73) Assignees: Toshio Miyata, Kanagawa (JP); Kiyoshi Kurokawa, Tokyo (JP); Tokai University Educational System, Tokyo (JP)

( * ) Notice: Subject to any disclaimer, the term of this patent is extended or adjusted under 35 U.S.C. 154(b) by 0 days.

(21) Appl. No.: 09/889,914
(22) PCT Filed: Jan. 27, 2000
(86) PCT No.: PCT/JP00/00413
§ 371 (c)(1), (2), (4) Date: Nov. 5, 2001
(87) PCT Pub. No.: WO00/44783
PCT Pub. Date: Aug. 3, 2000

(30) Foreign Application Priority Data

Jan. 29, 1999 (JP) .............................................. 11/21543

(51) Int. Cl.[7] ............................ C07K 17/00; C07K 1/00
(52) U.S. Cl. ........................ 530/350; 530/827; 530/835
(58) Field of Search ................................. 530/300, 350, 530/827, 835; 424/184.1; 514/2, 12

(56) References Cited

FOREIGN PATENT DOCUMENTS

| WO | WO 98/22501 | 5/1998 |
| WO | WO 98/45436 | 10/1998 |
| WO | WO 98/56804 | 12/1998 |

OTHER PUBLICATIONS

Coppola, M. et al., (2000), *Genomics*, 66:48–54.
Miyata, T. et al., (1998), *J. Clin. Invest.*, 120(4):828–836.
Patel, S and Latterich, M, (1998), *Cell Biology*, 8:65–71.
Zhang, Q–H, et al., (2000), Genome Research, 10:1546–1560.
EMBL Accession No. AA285032, Hillier et al., (Apr. 5, 1997).
EMBL Accession No. AJ132637, Coppola et al., (Aug. 2, 1999).
EMBL Accession No. AF070656, Zhang et al., (Mar. 24, 1999).
EMBL Accession No. AF090430, Butterworth et al., (Sep. 23, 1998).
SWALL Accession No. 088967, Butterworth et al., (Nov. 1, 1998).
Skolnick et al., Trends in Biotech., 18(1):34–39, 2000.*
Thorsness et al., Mol. Cell. Biol., 13:5418–5426, 1993.*
Schwarzlose et al., Yeast 10:1141–1155, 1994.*
Nakai et al., Mol. Cell. Biol., 15:4441–4452, 1995.*

* cited by examiner

*Primary Examiner*—Gary Kunz
*Assistant Examiner*—Sharon Turner
(74) *Attorney, Agent, or Firm*—Karl Bozicevic; Bozicevic, Field & Francis LLP

(57) ABSTRACT

The present invention provides a DNA expressed at high frequency in mesangial cells and a protein (Meg-4) encoded by this DNA. These substances are useful in, for example, identifying mesangial cells and detecting abnormalities in mesangial cells. Moreover, the above protein would be helpful for clarification of the functions of mesangial cells and, in its turn, for clarification of the causes of diseases relating to mesangial cells. This protein is expectedly applicable to the treatment, diagnosis, and such of diseases relating to mesangial cells.

2 Claims, 7 Drawing Sheets

FIG. 1A

```
ctatagggaa agctggtacg cctgcaggta ccggtccgga aattcgcggc cgcgtcgacg  -53
ggtgaggtcg ctgagggccc gccgggggtg aggtcgctga gggcccgccg gagatgtttt    7
ccttgtcgag cacggtgcaa ccccagttta cagttcctct gagtcatctc atcaatgcct   67
tccatacacc aaaaaacact tctgtttctc tcagtggagt gtcagtttct caaaaccagc  127
atcgagatgt agttcctgag catgaggctc ccagcagtga gtgtatgttc agtgacttcc  187
tgacgaagct taacattgtt tcaatcggca aaggaaaaat attcgaaggg tacagatcca  247
tgttcatgga gccagcaaaa aggatgaaga agagcttgga cacaaccgat aactggcaca  307
tccgtccaga accttctcc ctctcaatcc ctccttcact taacttaagg gaccttggat   367
tatctgaatt aaaaattgga cagattgatc agctggtaga aaatctactt cctggatttt  427
gtaaaggcaa aaacatttct tcccattggc atacatccca tgtctctgca caatccttct  487
ttgaaaataa atatggtaac ttagatatat ttagtacatt acgttcctct tgcttgtatc  547
gacatcattc aagagctctt caaagcattt gttcagatct tcagtactgg ccagttttca  607
tacagtctcg gggttttaaa actttgaaat caaggacacg acgtctccag tctacctccg  667
agagattagc tgaaacacag aatatagcgc catcattcgt gaagggtttt cttttgcggg  727
acagaggatc agatgttgag agtttggaca aactcatgaa aaccaaaaat atacctgaag  787
ctcaccaaga tgcatttaaa actggttttg cggaaggttt tctgaaagct caagcactca  847
cacaaaaaac caatgattcc ctaaggcgaa cccgtctgat tctcttcgtt ctgctgctat  907
tcggcattta tggacttcta aaaaacccat ttttatctgt ccgcttccgg acaacaacag  967
ggcttgattc tgcagtagat cctgtccaga tgaaaaatgt cacctttgaa catgttaaag 1027
gggtggagga agctaaacaa gaattacagg aagttgttga attcttgaaa aatccacaaa 1087
aatttactat tcttggaggt aaacttccaa aaggaattct tttagttgga cccccaggga 1147
ctggaaagac acttcttgcc cgagctgtgg cgggagaagc tgatgttcct ttttattatg 1207
cttctggatc cgaatttgat gagatgtttg tgggtgtggg agccagccgt atcagaaatc 1267
ttttttaggga agcaaaggcg aatgctcctt gtgttatatt tattgatgaa ttagattctg 1327
ttggtgggaa gagaattgaa tctccaatgc atccatattc aaggcagacc ataaatcaac 1387
ttcttgctga aatggatggt tttaaaccca atgaaggagt tatcataata ggagccacaa 1447
acttcccaga ggcattagat aatgccttaa tacgtcctgg tcgttttgac atgcaagtta 1507
cagttccaag gccagatgta aaaggtcgaa cagaaatttt gaaatggtat ctcrataaaw 1567
taaagtttga tcaatccgtt gatccagaaa ttatagctcg aggtactgtt ggcttttccg 1627
gagcagagtt ggagaatctt gtgaaccarg ctgcattaaa agcagctgtt gatggaaaag 1687
aaatggttac catgaaggag ctggagtttt ccaaagacaa aattctaatg gggcctgaaa 1747
gaagaagtgt ggaaattgat aacaaaaaca aaaccatcac agcatatcat gaatctggtc 1807
atgccattat tgcatattac acaaaagatg caatgcctat caacaaagct acaatcatgc 1867
cacgggggcc aacgcttgga catgtgtccc tgttacctga gaatgacaga tggaatgaaa 1927
ctagagccca gctgcttgca caaatggatg ttagtatggg aggaagagtg gcagaggagc 1987
ttatatttgg aaccgaccat attacaacag gtgcttccag tgattttgat aatgccacta 2047
aaatagcaaa gcggatggtt accaaatttg gaatgagtga aaagcttgga gttatgacct 2107
acagtgatac agggaaacta gtccagaaa cccaatctgc catcgaacaa gaaataagaa  2167
tccttctaag ggactcatat gaacgagcaa acatatcttt gaaaactcat gcaaaggagc 2227
ataagaatct cgcagaagct ttattgacct atgagacttt ggatgccaaa gagattcaaa 2287
ttgttcttga ggggaaaaag ttggaagtga gatgataact ctcttgatat ggatgcttgc 2347
tggttttatt gcaagaatat aagtagcatt gcagtagtct acttttacaa cgctttcccc 2407
tcattcttga tgtagtgtaa ttgaagggtg tgaaatgctt tgtcaatcat ttgtcacatt 2467
tatccagttt gggttattct cattatgaca cctattgcaa attagcatcc catggcaaat 2527
atatttgaa aaaataaaga actatcagga ttgaaaacag ctcttttgag gaatgtcaat  2587
```

(SEQ ID NO:1, Position -53 to 2587)

FIG. 1B

```
tagttattaa gttgaaagta attaatgatt ttatgtttgg ttactctact agatttgata 2647
aaaattgtgc ctttagcctt ctatatacat cagtggaaac ttaagatgca gtaattatgt 2707
tccagattga ccatgaataa aatatttttt aatctaaatg tagagaagtt gggattaaaa 2767
gcagcctcgg aaacacagag ccaggaatat agccttttgg catggtgcca tggctcacat 2827
ctgtaatccc agcacttttg gaggctgagg cgggtggatt gcttgaggcc aggagttcga 2887
gaccagcctg gccaacgtgg tgaaacgctg tctctactaa aatacaaaaa aatagggctg 2947
ggcgcggttg ctcacgcctg taatcccagc acttttcaga ggccaaggcg ggcaaatcac 3007
ctgaggtcaa gagtttgaga ccagcctggc caacatggtg aaaccccatc tctactaaac 3067
atgcaaaaat tacctgggca tggtggcagg tgcttataat cccagctact ctggggggca 3127
aggcaggaga attgcttgag cctgggagat ggaggttgca gtgagctgag atcatgccac 3187
tgcactccag cctgggcaac agagcaagac tctgcctcaa aaaaaaatta aaataaattt 3247
aaatacaaaa aaaaatagcc aggtgtgggg tgcatgcctg gaatcccagc tacttgagag 3307
gctgaggcac gagaattgct tgaacccagg aggtggaggt tgcagtgagc caagatcaca 3367
ggagccactg cactccagcc tgggtgacag agtgagactc tgtctcaaaa aaaaaattaa 3427
ataaattatt ataacctttc agaaatgctg tgtgcatttt catgttcttt tttttagcat 3487
tactgtcact ctccctaatg aaatgtactt cagagaagca gtatttgtt aaataaatac 3547
ataacctcat tctgaataat gtccctcatt ttgactataa ctgtgcttgg tttcaaaagc 3607
aaaattaaac aaaaatctca gtcccctccg aagtgaactt tgtgttaccc tgcgtcagaa 3667
atgccaagtt gtgtttactt ttcattcaga ttttgtgaat atgaacatgc tgttataqga 3727
tctacagatg aatatttaac tcaatagaaa aattatttta gaacacattg tattggtatt 3787
tacaaccaga ttatattctt gacgttgact tcattaaaat t              3828
(SEQ ID NO: 1, Position 2647 to 3828)
```

FIG. 1C

```
Met Phe Ser Leu Ser Ser Thr Val Gln Pro Gln Phe Thr Val Pro Leu
1               5                   10                  15
Ser His Leu Ile Asn Ala Phe His Thr Pro Lys Asn Thr Ser Val Ser
                20                  25                  30
Leu Ser Gly Val Ser Val Ser Gln Asn Gln His Arg Asp Val Val Pro
            35                  40                  45
Glu His Glu Ala Pro Ser Ser Glu Cys Met Phe Ser Asp Phe Leu Thr
    50                  55                  60
Lys Leu Asn Ile Val Ser Ile Gly Lys Gly Lys Ile Phe Glu Gly Tyr
65                  70                  75                  80
Arg Ser Met Phe Met Glu Pro Ala Lys Arg Met Lys Lys Ser Leu Asp
                85                  90                  95
Thr Thr Asp Asn Trp His Ile Arg Pro Glu Pro Phe Ser Leu Ser Ile
            100                 105                 110
Pro Pro Ser Leu Asn Leu Arg Asp Leu Gly Leu Ser Glu Leu Lys Ile
            115                 120                 125
Gly Gln Ile Asp Gln Leu Val Glu Asn Leu Leu Pro Gly Phe Cys Lys
    130                 135                 140
Gly Lys Asn Ile Ser Ser His Trp His Thr Ser His Val Ser Ala Gln
145                 150                 155                 160
Ser Phe Phe Glu Asn Lys Tyr Gly Asn Leu Asp Ile Phe Ser Thr Leu
                165                 170                 175
Arg Ser Ser Cys Leu Tyr Arg His His Ser Arg Ala Leu Gln Ser Ile
            180                 185                 190
Cys Ser Asp Leu Gln Tyr Trp Pro Val Phe Ile Gln Ser Arg Gly Phe
            195                 200                 205
Lys Thr Leu Lys Ser Arg Thr Arg Arg Leu Gln Ser Thr Ser Glu Arg
    210                 215                 220
Leu Ala Glu Thr Gln Asn Ile Ala Pro Ser Phe Val Lys Gly Phe Leu
225                 230                 235                 240
Leu Arg Asp Arg Gly Ser Asp Val Glu Ser Leu Asp Lys Leu Met Lys
                245                 250                 255
Thr Lys Asn Ile Pro Glu Ala His Gln Asp Ala Phe Lys Thr Gly Phe
            260                 265                 270
Ala Glu Gly Phe Leu Lys Ala Gln Ala Leu Thr Gln Lys Thr Asn Asp
            275                 280                 285
Ser Leu Arg Arg Thr Arg Leu Ile Leu Phe Val Leu Leu Leu Phe Gly
    290                 295                 300
Ile Tyr Gly Leu Leu Lys Asn Pro Phe Leu Ser Val Arg Phe Arg Thr
305                 310                 315                 320
Thr Thr Gly Leu Asp Ser Ala Val Asp Pro Val Gln Met Lys Asn Val
                325                 330                 335
Thr Phe Glu His Val Lys Gly Val Glu Glu Ala Lys Gln Glu Leu Gln
            340                 345                 350
Glu Val Val Glu Phe Leu Lys Asn Pro Gln Lys Phe Thr Ile Leu Gly
            355                 360                 365
(SEQ ID NO: 2, Position 1 to 368)
```

FIG. 1D

```
Gly Lys Leu Pro Lys Gly Ile Leu Leu Val Gly Pro Pro Gly Thr Gly
    370             375             380
Lys Thr Leu Leu Ala Arg Ala Val Ala Gly Glu Ala Asp Val Pro Phe
385             390             395             400
Tyr Tyr Ala Ser Gly Ser Glu Phe Asp Glu Met Phe Val Gly Val Gly
            405             410             415
Ala Ser Arg Ile Arg Asn Leu Phe Arg Glu Ala Lys Ala Asn Ala Pro
            420             425             430
Cys Val Ile Phe Ile Asp Glu Leu Asp Ser Val Gly Gly Lys Arg Ile
            435             440             445
Glu Ser Pro Met His Pro Tyr Ser Arg Gln Thr Ile Asn Gln Leu Leu
450             455             460
Ala Glu Met Asp Gly Phe Lys Pro Asn Glu Gly Val Ile Ile Ile Gly
465             470             475             480
Ala Thr Asn Phe Pro Glu Ala Leu Asp Asn Ala Leu Ile Arg Pro Gly
            485             490             495
Arg Phe Asp Met Gln Val Thr Val Pro Arg Pro Asp Val Lys Gly Arg
            500             505             510
Thr Glu Ile Leu Lys Trp Tyr Leu Asx Lys Xaa Lys Phe Asp Gln Ser
            515             520             525
Val Asp Pro Glu Ile Ile Ala Arg Gly Thr Val Gly Phe Ser Gly Ala
            530             535             540
Glu Leu Glu Asn Leu Val Asn Gln Ala Ala Leu Lys Ala Ala Val Asp
545             550             555             560
Gly Lys Glu Met Val Thr Met Lys Glu Leu Glu Phe Ser Lys Asp Lys
                565             570             575
Ile Leu Met Gly Pro Glu Arg Arg Ser Val Glu Ile Asp Asn Lys Asn
            580             585             590
Lys Thr Ile Thr Ala Tyr His Glu Ser Gly His Ala Ile Ile Ala Tyr
            595             600             605
Tyr Thr Lys Asp Ala Met Pro Ile Asn Lys Ala Thr Ile Met Pro Arg
            610             615             620
Gly Pro Thr Leu Gly His Val Ser Leu Leu Pro Glu Asn Asp Arg Trp
625             630             635             640
Asn Glu Thr Arg Ala Gln Leu Leu Ala Gln Met Asp Val Ser Met Gly
            645             650             655
Gly Arg Val Ala Glu Glu Leu Ile Phe Gly Thr Asp His Ile Thr Thr
            660             665             670
Gly Ala Ser Ser Asp Phe Asp Asn Ala Thr Lys Ile Ala Lys Arg Met
            675             680             685
Val Thr Lys Phe Gly Met Ser Glu Lys Leu Gly Val Met Thr Tyr Ser
            690             695             700
Asp Thr Gly Lys Leu Ser Pro Glu Thr Gln Ser Ala Ile Glu Gln Glu
705             710             715             720
Ile Arg Ile Leu Leu Arg Asp Ser Tyr Glu Arg Ala Lys His Ile Leu
            725             730             735
Lys Thr His Ala Lys Glu His Lys Asn Leu Ala Glu Ala Leu Leu Thr
            740             745             750
Tyr Glu Thr Leu Asp Ala Lys Glu Ile Gln Ile Val Leu Glu Gly Lys
755             760             765
Lys Leu Glu Val Arg
    770        (SEQ ID NO: 2, Position 369 to 773)
```

——————— ATP binding motif     ▭ Minimum AAA protein motif

— - — - — - — walker B binding motif     ▭ Zn binding motif

10

MEG-4 PROTEIN

TECHNICAL FIELD

The present invention belongs to the field of genetic engineering and specifically relates to isolation of a gene of renal cells.

BACKGROUND ART

Sixty trillion various cells in vivo essentially comprise identical genomic DNA. For the normal physiological functions, the expression of these genes is strictly controlled by signals received by cell lines and cells. Therefore, elucidation of genes expressed in each cell type is very important.

A mesangial cell plays a pivotal role in maintaining the structure and function of a glomerulus and also has a central meaning of pathophysiology for each type of nephritis. For example, proliferation of mesangial cells and accumulation of extracellular mesangial matrix are thought to be important pathological finding of glomerulosclerosis in a patient suffering from various glomerular diseases such as chronic nephritis and diabetic nephropathy.

Therefore, identification of genes expressed specifically in mesangial cells and elucidation of its function are helpful for understanding biological characteristics of mesangial cells and the causes of diseases relating to mesangial cells, and in turn, treating or diagnosing diseases relating to mesangial cells.

Thy1 antigen is known as a marker for mesangial cells in rats. However, this gene is not specific to mesangial cells and is not expressed in human mesangial cells (Miyata T. et al., Immunology, 1989,67: 531–533; and Miyata T. et al., Immunology, 1990, 69: 391–395). Mesangial cells are known to express α smooth muscle actin when activated, but this gene is also not specific to mesangial cells. Any genes characteristically in mesangial cells have not been reported.

The present inventor has previously reported MEGSIN as a protein that is expressed specifically in the mesangial cells (J. Clin. Invest, Aug. 15, 1998 102: 4, 828–36). The present invention relates to a novel protein having a structure that is distinctly different from the MEGSIN.

DISCLOSURE OF THE INVENTION

An objective of the present invention is to isolate a gene highly expressed in mesangial cells.

The current inventor isolated mRNA from in vitro cultures of human mesangial cells to construct a cDNA library of 3' side. Sequences of numerous clones were randomly determined from the cDNA library and compared with the known nucleotide sequences of cDNA clones of 3' side obtained from various organs and cells to determine the clones expressed in mesangial cells. One of the clones, which appeared with high frequency in the mesangial cells, was selected. Furthermore, the λZIPLox cDNA library prepared from mesangial cells using the insert of this clone as a probe was screened to determine the nucleotide sequence of the positive clone. Based on the determined cDNA nucleotide sequence, the amino acid sequence of the longest open reading frame was elucidated. Several characteristic motifs were found in this amino acid sequence. Since homology was confirmed with mouse ATP dependent metalloprotease (ATP-MP), a known protein, this amino acid sequence was presumed to be the amino acid sequence of the protein encoded by the cDNA of this invention. The protein of this invention having this amino acid sequence was named Meg-4by the present inventor. The nucleotide sequence of human Meg-4 cDNA and the deduced amino acid sequence for human Meg-4 are shown in SEQ ID NO: 1 and SEQ ID NO: 2, respectively.

An amino acid sequence homology search performed on this amino acid sequence using the SwissProt database confirmed that Meg-4 is a novel protein containing an AAA motif (Walker, J. E. et al., EMBO J. 1982, 8: 945–951; Swaffield, J. C. et al., Nature, 374: 88–91; Fry, D. C. et al., Proc. Natl. Acad. Sci. USA. 1997, 83: 907–911; Frohlich, K. U. et al., J. Cell. Biol. 1991, 114:443–453) characteristic of AAA protein family (ATPases associated with different cellular activities protein family). Furthermore, when the topography of Meg-4 was observed by Northern blotting, expression of Meg-4 was hardly observed in the human lung and liver, and expression was observed in the kidney as well as in other tissues, such as the heart, brain, placenta, skeletal muscle, and pancreas. At the cellular level, especially high levels of expression in the mesangial cells was characteristic. Expression was also observed in fibroblasts and epithelial cells. This invention was completed based on these findings.

This invention specifically includes the following:

(1) A protein comprising the amino acid sequence of SEQ ID NO: 2, or a protein comprising the amino acid sequence of SEQ ID NO: 2 in which one or more amino acids are replaced, deleted, added, and/or inserted, and being functionally equivalent to the protein comprising the amino acid sequence of SEQ ID NO: 2.

(2) The protein of (1), wherein the protein comprises an amino acid sequence that has not less than 90% homology to the amino acid sequence of SEQ ID NO: 2.

(3) The protein of (1), wherein the protein comprises the amino acid sequence of SEQ ID NO: 2.

(4) A DNA encoding the protein of (1).

(5) The DNA of (4), wherein the DNA comprises a nucleotide sequence that has not less than 85% homology to the nucleotide sequence of SEQ ID NO: 1.

(6) The DNA of (5), wherein the DNA comprises a protein coding region in the nucleotide sequence of SEQ ID NO: 1.

(7) A DNA encoding the protein of (1), the DNA hybridizing under stringent conditions with DNA comprising the nucleotide sequence of SEQ ID NO: 1.

(8) A DNA hybridizing specifically with a DNA comprising the nucleotide sequence of SEQ ID NO: 1 or with the complementary strand thereof, the DNA having a chain length of at least 15 nucleotides.

(9) An antisense DNA against the DNA of (6) or a portion thereof.

(10) A vector comprising the DNA of any one of (4), (5), (6), and (7).

(11) A transformant expressively carrying the DNA of any one of (4) (5), (6), and (7).

(12) A method for producing the protein of (1), the method comprising culturing the transformant of (11) and collecting an expression product of the DNA of any one of (4), (5), (6), and (7).

(13) An antibody binding to the protein of (1).

(14) The antibody of (13), wherein the antibody recognizes a protein comprising an amino acid sequence selected from the amino acid sequence of SEQ ID NO: 2.

(15) The antibody of (14), wherein the antibody is a monoclonal antibody.

(16) An immunoassay method for measuring the protein of (3) or a fragment thereof based on immunological binding of the antibody of (14) or (15) to the protein of (2) or a fragment thereof.

(17) A reagent for an immunoassay for the protein of (3) or a fragment thereof, the reagent comprising the antibody of (14) or (15).

(18) A method for detecting mesangial proliferative nephropathy, the method comprising measuring the protein of (3) or a fragment thereof contained in a biological sample and comparing the measured value with that obtained from a normal sample.

(19) A transgenic nonhuman vertebrate in which the expression level of a gene encoding Meg-4 is modified.

(20) The transgenic nonhuman vertebrate of (19), wherein the nonhuman vertebrate is a mouse.

(21) The transgenic nonhuman vertebrate of (20), wherein the nonhuman vertebrate is a knockout mouse in which the expression of a gene encoding Meg-4 is inhibited.

To fulfill the issues mentioned above, the present inventor used a 3'-directed CDNA library. This method avoids the effect of the size of cDNA on cloning efficiency. The sequence at the 3' region characterizes each of the genes, and the sequence data of approximately 200 to 300 bp are large enough to demonstrate the characteristics of the gene.

The DNA encoding human Meg-4 of the present invention can be obtained by preparing mRNA from mesangial cells and converting them to the double stranded cDNA by the known methods. mRNA can be prepared by, for example, the guanidine isothiocyanate-cesium chloride method (Chirwin, et al., Biochemistry 18, 5294, 1979), and the treatment with a surfactant and phenol in the presence of deoxyribonuclease (Berger & Birkenmeier, Biochemistry 18, 5143, 1979), etc. Poly(A)$^+$ RNA can be prepared from total RNA by, for example, the affinity chromatography using such a carrier bound to oligo(dT) as Sepharose, cellulose, latex particles, etc. A hybrid strand made of the mRNA obtained and its complementary DNA (cDNA) can be obtained by using the mRNA as a template, and treating it with reverse transcriptase using, as a primer, oligo(dT) complementary to the poly(A) strand at the 3'-end, a random primer, or a synthetic oligonucleotide corresponding to a portion of the Meg-4 amino acid sequence. This mRNA strand can be converted to a double stranded cDNA by treating it with, for example, E. coli RNase H, E. coli DNA polymerase I, and E. coli DNA ligase and by replacing the mRNA with a DNA strand.

The DNA can be cloned by RT-PCR method using poly (A)$^+$ RNA from mesangial cells as a template, and primers synthesized based on the human Meg-4 gene nucleotide sequence. Alternatively, without using PCR, the target cDNA can be obtained by directly screening a cDNA library with a probe synthesized based on human Meg-4 gene nucleotide sequence. The gene of the present invention can be selected by confirming the nucleotide sequence of the gene among the genes obtained by these methods.

In addition, for example, as Example 8 shows, the cDNA library of human mesangial cells can be used as a template to isolate the Meg-4 phenotype as shown in SEQ ID NO: 7. Such phenotype is included in Meg-4 of this invention. The Meg-4 cDNA homologues in species other than humans, such as mouse or rat, can be obtained using similar methods.

Furthermore, the Meg-4 cDNA homologues can be isolated as follows. The cDNA encoding the Meg-4 homologue can be isolated by screening the cDNA library by colony hybridization and plaque hybridization, using the nucleotide sequence of the above-mentioned human Meg-4 cDNA as a probe. The cDNA library can be synthesized by using mRNA isolated from mouse or rat tissues, cultured mesangial cells, and the like as template. A commercially available cDNA library (Funakoshi, and the like) may also be used. PCR that utilizes a degenerative primer, which is designed to be placed before and after ORF, based on the cDNA of human Meg-4 of this invention is another possible method that amplifies the cDNA of homologues.

Although the AAA protein family shares the AAA motif, the sequences in the other regions are not necessarily similar. However, in homologues such as mouse ATP-MP, which will be mentioned later, for example, a certain degree of similarity exists in regions other than the AAA motif, and amplification by PCR is possible. The inventor has confirmed that, other than with mouse, amplification of Meg-4 homologue cDNA fragments by degenerative primer is possible with rat.

The human Meg-4 genome can be obtained by screening a genomic library. A genomic library can be synthesized, for example, by preparing a genome from human B lymphoblasts and by inserting, into phage vector EMBL3, DNAs partially digested with Sau3 (Blood, vol 83, No 11, 1994: pp3126–3131). A clone containing the desired genome can be obtained by performing plaque hybridization (see, Shin Saibou Kougaku Jikken (New Cell Biotechnology Experiment) Protocols, Shujun-sha, pp79–92) for such a genomic library. The entire open reading frame region of Meg-4 cDNA (2322 bp), or each of the exon-intron portions obtained by amplifying the human genomic DNA by PCR method using part of the cDNA as primers can be used as probes. As it will be mentioned later, since the Meg-4 gene is mapped on the short arm of chromosome 10 at 10 p11.23–12.1., the human Meg-4 genome is easily isolated from a genomic clone containing this region.

A sequence of 5' UTR of the control region sequence can be determined by 5' RACE method (5'-Full RACE Core Set, following Takara's protocol) using human cultured mesangial cell-derived mRNA or human renal mRNA (purchased from Clontech) as a template.

The gene of the present invention can also be produced by following the standard methods using chemical synthesis of nucleic acids, such as phosphoamidite method (Mattencci, M. D. & Caruthers, M. H. J. Am. Chem. Soc. 103, 3185, 1981), phosphite triester method (Hunkapiller, M. et al., Nature 310, 105, 1984).

An eukaryotic gene often shows polymorphism, like human interferon gene, and one or more amino acids may be replaced by this polymorphism with generally maintaining activities of a protein. In general, activities of proteins can be often maintained even if one or more amino acids are modified. Therefore, gene encoding a protein obtained by using the artificially modified gene encoding an amino acid sequence of SEQ ID NO: 2 is included in this invention as long as the protein possesses the function typical to the gene of the present invention. The present invention includes protein in which an amino acid sequence of SEQ ID NO: 2 is artificially modified as long as it has characteristics of the proteins of the present invention.

The proteins of the present invention comprise the amino acid sequence of SEQ ID NO: 2 or the amino acid sequence in which one or more amino acids are replaced, deleted, added, and/or inserted, and being functionally equivalent to Meg-4 protein of present invention. In this invention, "functionally equivalent" means having biological properties that are the same as Meg-4. The inventor has found the following biological properties in Meg-4, for example.

Structurally, Meg-4 belongs to the AAA protein family. Here, the AAA protein family refers to proteins that have $Mg^{2+}$-dependent ATPase activity, an AAA motif with highly conserved 230 to 250 bases (including the ATP binding motif, minimum AAA protein motif, and walker B motif), and a metal binding motif (HEXXH). Several ATP-MPs are known to be AAA proteins. However, their cellular localization varies.

Varieties of functions have been reported, such as cell cycle regulation, protein degradation, organellar biosynthesis, and protein transport.

The characteristics of Meg-4 expression are that the expression is high in kidney mesangial cells, that it has been observed in tissues such as the kidney, heart, brain, placenta, skeletal muscles, and pancreas, and that it has been observed to be weak in the lungs and liver. Furthermore, in cultured cancer cell lines, marked expression of Meg-4 is not observed. The expression of Meg-4 in each of the tissues can be known by performing a Northern blot assay using mRNA prepared from each of the tissues as samples, and using, for example, the nucleotide sequence selected from SEQ ID NO: 1 as a probe.

All proteins that are functionally equivalent with regard to the biological properties mentioned above compose Meg-4 of this invention. Therefore, this invention includes not only human Meg-4, whose structure is specifically elucidated, but also other homologues equivalent in terms of structure or function.

In this invention, an amino acid sequence of SEQ ID NO: 2 in which one or more amino acids are replaced, deleted, added, and/or inserted is preferably a sequence that has not less than 90% homology as a whole to the amino acid sequence of SEQ ID NO: 2. Amino acid sequence homology can be determined by FASTA. More specifically, sequences where 1 to 50, preferably 1 to 10 amino acids are replaced with other amino acids, deleted, added, or inserted in the amino acid sequence indicated in SEQ ID NO: 2.

The DNA of the present invention includes DNAs encoding these functionally equivalent proteins. The DNAs encoding these proteins can be cDNA, genomic DNA, or synthetic DNA.

The codons for desired amino acids themselves are well-known, can be optionally selected, and can be determined by following the standard method by, for example, considering the frequency of use of codons in hosts to be used (Grantham, R. et al. Nucleic Acids Res. 9, r43, 1981). Therefore, the present invention includes DNAs appropriately modified by degeneration of codons. It is possible to partially change the codons of these nucleotide sequences by following site-specific mutagenesis methods (Mark, D. F. et al., Proc. Natl. Acad. Sci. U.S.A. 1984, 81: 5662) and such that uses chemically synthesized oligonucleotides encoding the desired modifications as primers.

A DNA hybridizing with a DNA containing the nucleotide sequence of SEQ ID NO: 1 and encoding a protein that typically functions as Meg-4 of the present invention, can be included in the DNA of the present invention. A sequence capable of hybridizing with specific sequences under stringent conditions is thought to have the activities similar to a protein encoded by the specific sequences. Stringent conditions generally indicate the following conditions. That is, hybridization is carried out at 65° C. in 4×SSC, and then washing is carried out for one hour at 65° C. using 0.1×SSC. The temperature of hybridization and washing, which greatly affect stringency, can be adjusted depending on the melting temperature (Tm). Tm changes, depending on the proportion of constituent bases occupying the base pairs to be hybridized, and by the composition of the hybridization solution (salt concentration, concentrations of formamide and sodium dodecyl sulfate). Therefore, through experience, one skilled in the art can consider these conditions mentioned above to set appropriate conditions that will yield similar stringency. The DNA of this invention includes DNA comprising the nucleotide sequence having preferably not less than 85% and more preferably not less than 95% sequence homology, according to homology search by FASTA and BLAST, to the nucleotide sequence indicated in SEQ ID NO: 1.

The nucleotide sequences of DNAs of the present invention, including mutants, can be used for various purposes based on known techniques.

Other prokaryotic or eukaryotic hosts can be transformed by inserting the gene encoding Meg-4 cloned as described above into an appropriate expression vector DNA. Moreover, the gene can be expressed in each host cell by introducing an appropriate promoter and sequences relating to the phenotypic expression into the expression vector. As an expression vector, for example, pET-3 (Studier & Moffatt, J. Mol. Biol. 189, 113, 1986) and such for *E. coli*, pEF-BOS (Nucleic Acids Research 18, 5322, 1990), pSV2-gpt (Mulligan & Berg, Proc. Natl. Acad. Sci. U. S. A. 78, 2072, 1981), and so on for COS cells, and pVY1 (WO89/03874) and such for CHO cells can be used. The target proteins can be expressed as a fusion protein derived from a fusion gene between a target gene and a gene encoding other polypeptide. Such fusion proteins can easily be purified and separated to isolate a desired protein. Histidine tag, c-myc tag, MBP-tag, GST-tag, and the like are known as proteins to be fused. Vectors that can express inserts in which these tags are fused are commercially available.

For example, *Escherichia coli* can be used as prokaryotic host cells in the expression system of the present invention. *Saccharomyces cerevisiae* and such can be used as microbiological host cells among eukaryotic organisms. Examples of mammalian host cells include COS cells, CHO cells, BHK cells, etc. The transformants of the current invention can be cultured under appropriately selected culturing condition suitable for host cells.

As mentioned above, Meg-4 can be produced by culturing the trans formants transformed with the gene encoding the target Meg-4, and recovering it from the cells or the culture supernatant. It can be purified into a substantially pure protein. Meg-4, a target protein of the present invention, can be separated and purified by the separation and purification methods commonly used for proteins, and the method is not particularly limited. Meg-4 can be separated and purified by, for example, appropriately selecting and combining various chromatographies.

Besides the methods described above, the gene of the present invention, the recombinant vector comprising the gene, the transformants carrying the vector, and the production of Meg-4 using gene manipulation can be manipulated by the standard method described in "Molecular Cloning—A Laboratory Manual" (Cold Spring Harbor Laboratory, N. Y.).

In addition, a probe for detecting a Meg-4 gene can be designed based on the nucleotide sequence of SEQ IN NO: 1. Moreover, primers for amplifying DNA and RNA containing these nucleotide sequences can be designed. It is routine for a person skilled in the art to design probes and primers based on a given sequence. An oligonucleotide comprising a designed nucleotide sequence can be chemically synthesized. These oligonucleotides can be used for the hybridization assay of various formats, or for the synthetic reaction of nucleic acids, such as PCR, if appropriately labeled. An oligonucleotide used as a probe or a primer has at least 15 bases, and preferably 25 to 50 bases.

Furthermore, an antisense nucleic acid that may regulate the expression of Meg-4 is provided based on the nucleotide sequence of the gene encoding Meg-4 disclosed in this invention. The antisense nucleic acid of this invention is an important tool for demonstrating the role of Meg-4 in the mesangial cells. It is also useful for regulating diseased conditions caused by accelerated expression of Meg-4. The effects of inhibiting the expression of target genes by antisense nucleic acids are the following. They are inhibition of transcription initiation by triple strand formation, transcription inhibition by hybrid formation with a site that has formed a local open loop structure due to RNA polymerase, transcription inhibition by hybrid formation with RNA that is being synthesized, splicing inhibition by hybrid formation at the joint between intron and exon, splicing inhibition by hybrid formation with the spliceosome forming region, inhibition of mRNA transition from the nucleus to the cytoplasm by hybrid formation with mRNA, splicing inhibition by hybrid formation with the capping region and the poly(A) attached region, inhibition of translation initiation by hybrid formation with the translation initiation factor binding region, translation inhibition by hybrid formation with the ribosome binding region near the initiation codon, interception of protein chain elongation by hybrid formation with the translation region of mRNA and polysome binding region, and inhibition of gene expression by hybrid formation with the nucleic acid-protein interacting region, and the like. These inhibit the expression of the target gene by inhibiting the transcription, splicing, or translation processes (Hirashima and Inoue, Shin Seikagaku Jikken Koza 2 Kakusan IV Idenshi no Fukusei to Hatsugen (New Biochemistry Laboratory Experiment 2 Nucleic Acids IV Replication and Expression of Genes) Japanese Biochemical Society Edition, Tokyo Kagaku Doj in, pp. 319–347, 1993).

The antisense sequence used in this invention may inhibit the expression of the target genes by any one of the effects mentioned above. In one embodiment, if an antisense sequence complementary to the non-translational region located near the 5' end of mRNA of the gene is designed, it may be effective for inhibiting the translation of the gene. However, sequences complementary to the coding region or to the 3' end non-translational region may also be used. In this manner, the antisense DNA utilized in this invention includes DNA containing the antisense sequence of not only the translational region of the gene, but also the sequence of the non-translational region. The antisense DNA to be utilized is inserted downstream of the appropriate promoter, and preferably, a sequence including a transcription-terminating signal is inserted to the 3' end. DNA prepared in this manner can be transformed into the desired host by known methods. Preferably, the antisense DNA sequence should contain a sequence that is complementary to the endogenous gene (or its homologous genes) of the host to be transformed or its portion. However, as long as gene expression is inhibited effectively, complete complementarity is not necessary.

The RNA that is transcribed using antisense DNA as template is designed to have preferably 90% and most preferably 95% complementarity to the transcription product of the target gene. The length of the antisense DNA used for effectively inhibiting the expression of target genes is at least 15 nucleotides or more, preferably 100 nucleotides or more, and more preferably 500 nucleotides or more. Usually, the length of the antisense RNA used is shorter than 2.5 kb.

A promoter region and an enhancer region of Meg-4 gene existing in genome can be obtained based on the cDNA nucleotide sequence of Meg-4 of the present invention. As a result of in situ hybridization, the Meg-4 gene was mapped on the short arm of chromosome 10 at the 10p11.23–12.1. region (FIG. 4). Therefore, based on a known method, the promoter region and enhancer region of the Meg-4 gene can be obtained from the genomic clone that includes the region upstream from this region.

Specifically, these control regions can be obtained by the same method as described in unexamined published Japanese patent application (JP-A) No. Hei 6–181767; The Journal of Immunology, 1995, 155, 2477–2486; Proc. Natl. Acad. Sci. USA, 1995, 92, 3561–3565; etc. Herein, a promoter region means DNA region existing upstream of a transcription initiation site to control the expression of a gene, and an enhancer region means DNA region existing in an intron or 3' UTR to control expression of a gene.

Specifically, a promoter region can be obtained, for example, by the following method.

1) A promoter region of Meg-4 is cloned from a human genomic library using 5' end site of cDNA of Meg-4 as a probe.

2) Meg-4 gene is digested with restriction enzyme to obtain a DNA comprising the promoter region at the upstream region (2 to 5 kbp) containing a translation initiation codon of Meg-4 gene and determine the nucleotide sequence. The transcription initiation site (+1) is determined using poly (A) $^+$RNA prepared from human mesangial cells as a template, by the primer elongation method using primer DNA selected from cDNA sequence at 5' end site of Meg-4 gene. A site possibly comprising the promoter activity is predicted by searching transcription factor binding sequence from the nucleotide sequence.

3) The DNA fragment excluding the coding region of Meg-4 gene from the DNA obtained in 2) is subcloned in a plasmid, and a chloramphenicol acetyl transferase (CAT) gene or a luciferase gene is ligated as a reporter gene at 2 to 5 kbp downstream of the DNA fragment to construct a reporter plasmid. Similarly, DNA fragments corresponding to various sites upstream of Meg-4 gene, in which 5' and 3' end sites are stepwise removed, are prepared by digestion with restriction enzymes or by PCR to include possible promoter regions. The CAT gene or the luciferase gene is ligated as a reporter gene at downstream of these DNA fragments to construct a reporter plasmid.

4) A promoter region upstream of Meg-4 gene is obtained by measuring CAT or luciferase activity in animal cells transformed with the reporter plasmid prepared in 3).

A 3' UTR and an enhancer region in introns can be obtained by cloning genomic genes of human Meg-4 from a human genomic library using Meg-4 cDNA as a probe in the same manner as described above for the promoter.

Transcription factors controlling the expression of Meg-4 gene can be obtained by the known methods, for example, those described in "Shin Saibou Kougaku Jikken (New Cell Biotechnology Experiment) Protocols, Shujun-sha," "Biomanual series 5 Tensha Inshi Kenkyu-hou (studies on transcription factors), Yodo-sha," "DNA & Cell Biology, 13, 731–742, 1994," such as affinity chromatography, Southwestern method, footprinting method, gel shift method, or one-hybrid method. Herein, a transcription factor means a factor controlling the transcription of Meg-4 gene, including a transcription initiation factor that induces the transcription initiation reaction and a transcription control factor that up- or downregulates transcription.

Affinity chromatography can be performed by applying a nucleic extract to an affinity column in which promoter and enhancer regions obtained above are immobilized on Sepharose or latex beads, washing the column, eluting the binding transcription factor using a DNA comprising the same sequence as that immobilized in the column, and recovering the transcription factor controlling the expression of Meg-4 gene.

In the case of South-western method, cDNA is inserted into an *E. coli* expression vector such as λgt11, to synthesize a fusion protein with β-galactosidase. The fusion protein is adsorbed on a nitrocellulose membrane, and a phage which synthesizes the fusion protein showing binding activities is selected using radiolabeled DNA fragments of promoter and enhancer regions as probes to obtain the transcription factor controlling the expression of Meg-4 gene.

The gel shift method is based on the phenomenon that electrophoretic mobility on a polyacrylamide gel of DNA changes when it is bound to a protein. DNA fragments of the promoter region and enhancer region are used as probes and upon mixing with samples containing transcription factors (for example, nuclear protein extract), they are analyzed by electrophoresis under low ionic strength. The binding of transcription factors is detected as a band with mobility different from that of free DNA. The gel shift method allows separation of transcription factors from a mixture of proteins with high sensitivity.

Upon further analysis by the footprint method, the DNA-transcription factor complex obtained by the gel shift method allows determination of the transcription factor-binding site. The footprint method utilizes the phenomenon that when a protein binds to DNA, it is protected from DNase I digestion. That is, DNA of the promoter region and enhancer region labeled at the end with $^{32}p$ is partially digested by DNase I in the presence of transcription factors, and then separated by degenerate polyacrylamide gel used for determining nucleotide sequences. Comparison to the result when the same treatment is carried out in the absence of a transcription factor shows the disappearance of a band due to transcription factor binding, and therefore, estimation of the binding region becomes possible.

The present invention also provides an antibody recognizing Meg-4. The antibody of the present invention includes, for example, an antibody against the protein comprising the amino acid sequence of SEQ ID NO: 2. An antibody (for example, a polyclonal antibody, a monoclonal antibody) or an antiserum against Meg-4 or a partial peptide of Meg-4 of the present invention can be produced by a known method for producing an antibody and antiserum, using Meg-4 of the present invention, a partial peptide of Meg-4 of the present invention, or a fusion protein such as c-myc-(His)$_6$-Tag-Meg-4 or MBP-Meg-4 of the present invention as a antigen. More specifically, a peptide that has low sequence homology to other AAA family proteins and that includes a hydrophilic amino acid sequence is useful as an antigen. As confirmed by the Example, the amino acid sequence, KDKILMGPERRSVEIDNKNK (SEQ ID NO: 9), in the amino acid sequence of SEQ ID NO: 2 corresponds to the 574–593 position and is used as an antigen to obtain Meg-4 specific antibodies. A monoclonal antibody can be produced by, for example, the following method.

The Meg-4 of the present invention or a partial peptide of Meg-4 of the present invention is administered with well-known carrier or diluent to a warm-blooded animal at the site capable of producing an antibody. To enhance the antibody productivity, the complete Freund's adjuvant or incomplete Freund's adjuvant can be administered together with the antigen. Immunization is performed every one to six weeks, a total of about 2 to 10 times, in general. Warm-blooded animals to be used are, for example, a monkey, rabbit, dog, guinea pig, mouse, rat, sheep, goat, and domestic fowl, and preferably a mouse and rat.

Monoclonal antibody-producing cells can be prepared by selecting immunized warm-blooded animals, such as mice, in which an antibody titer is detected, obtaining spleen or lymph node from the animals 2 to 5 days after the final immunization, and fusing the antibody producing cells contained in these tissues with myeloma cells to obtain monoclonal antibody-producing hybridoma. The antibody titer in antiserum can be measured by, for example, reacting the labeled Meg-4 described below with antiserum, and measuring an activity of the label binding to the antibody. Cell fusion can be performed by a known method, for example, the method of Kohler and Milstein (Nature, 256, 495, 1975). Polyethylene glycol (PEG), Sendai virus, and such can be used as a fusion enhancer, and PEG is preferable.

Examples of myeloma cells include X-63Ag8, NS-1, P3U1, SP2/0, AP-1, etc., and X-63Ag8 is preferably used. The ratio of the number of antibody-producing cells (splenic cells) to that of myeloma cells is 1:20 to 20: 1. Cells can be fused efficiently by adding PEG (preferably PEG1000 to PEG6000) at the concentration of about 10 to 80%, and incubating for 1 to 10 min at 20 to 40° C., preferably at 30 to 37° C. Anti-Meg-4 antibody-producing hybridoma can be screened by various methods, for example, the method in which the hybridoma culture supernatant is added to a solid phase (for example, a microplate) on which Meg-4 antigen is adsorbed directly or with a carrier, and anti-immunoglobulin antibody labeled with a radioactive substance, an enzyme, and such (When cells used for cell fusion are derived from a mouse, anti-mouse immunoglobulin antibody is used.) or protein A is added thereto, and anti-Meg-4 monoclonal antibody binding to the solid phase is detected, the method in which the hybridoma culture supernatant is added to a solid phase on which anti-immunoglobulin antibody or protein A is adsorbed, and Meg-4 labeled with a radioactive substance, an enzyme, and such is added thereto, and anti-Meg-4 monoclonal antibody binding to the solid phase is detected.

Anti-Meg-4 monoclonal antibody can be selected and cloned by known methods or modified methods thereof using usually a culture medium for animal cells supplemented with HAT (hypoxanthine, aminopterin, and thymidine). Any medium for selection, cloning, and culturing can be used as long as hybridoma can grow therein. For example, RPMI 1640 medium (Dainippon Pharmaceutical Co., Ltd.) containing 1 to 20%, preferably 10 to 20% of fetal bovine serum, GIT medium (Wako Pure Chemicals) containing 1 to 10% fetal bovine serum, or serum-free medium for hybridoma culturing (SFM-101, Nissui Pharmaceutical Co., Ltd.) can be used. Incubation temperature is generally 20 to 40° C., preferably about37° C. Incubationtime is generally 5 days to 3 weeks andpreferably 1 to 2 weeks. Incubation is performed under the 5% carbon dioxide gas in general. The antibody titer of the hybridoma culture supernatant can be determined in the same manner as described above for the measurement of anti-Meg-4 antibody titer in the antiserum. Cloning can be generally conducted by known methods, for example, semisolid agar method, or limiting dilution method. A cloned hybridoma is cultured preferably in a serum-free medium, thereby producing an optimal amount of an antibody in the supernatant. Preferably, a target monoclonal antibody can be obtained in ascites.

A monoclonal antibody of the present invention does not crossreact with other proteins other than Meg-4 by selecting those capable of recognizing epitopes specific to meg-4. In general, an epitope specific to a protein is composed of at least 7 or more continuous amino acid residues, preferably 10 to 20 amino acids in an amino acid sequence of the protein. Therefore, amonoclonal antibodyrecognizing an epitope composed of peptides having an amino acid sequence selected from the amino acid sequence of SEQ ID NO: 2 and composed of at least 7 continuous amino acid residues can be the monoclonal antibody specific to Meg-4 of the present invention.

An anti-Meg-4 monoclonal antibody can be separated and purified by the separation and purification method of immunoglobulin commonly used for the separation and purification of polyclonal antibodies. The known purification methods include, for example, salting out, alcohol precipitation, isoelectric point precipitation, electrophoresis, adsorption and desorption method by ion exchanger (for example, DEAE) ultra centrifugation, gel filtration, or specific purification method whereby antibody is exclusively collected by, for example, an antigen binding solid phase or active adsorbent, such as Protein A or Protein G, and the binding is dissociated to obtain the antibody.

Monoclonal antibodies and polyclonal antibodies recognizing Meg-4 of the present invention, obtained in such a manner, can be used for the diagnosis and treatment for diseases relating to mesangial cells. Examples of a method for measuring Meg-4 with these antibodies include an sandwich assay comprising reacting Meg-4 with an antibody binding to an insoluble carrier and a labeled antibody and detecting Meg-4 in the sandwiched complex produced by the reaction, or a competition method comprising competitively reacting labeled human Meg-4 and human Meg-4 in a sample with an antibody to measure human Meg-4 in a samples based on labeled antigen amount reacted with the antibody.

The measurement of human Meg-4 by the sandwich method is conducted by, for example, the 2 step method in which an immobilized antibody is reacted with Meg-4, unreacted materials are completely removed by washing, and a labeled antibody is added to form a complex of the immobilized antibody Meg4-the labeled antibody, or one step method in which the immobilized antibody, the labeled antibody, and Meg-4 are mixed at the same time.

Examples of an insoluble carrier used for the measurement include, for example, polystyrene, polyethylene, polypropylene, polyvinyl chloride, polyester, polyacrylate, nylon, polyacetal, synthetic resin such as flourideresin, etc., polysaccharides such as cellulose, agarose, etc., glass, metals, etc. The form of an insoluble carrier can be varied and includes tray, spheroid, particle, fiber, stick, board, container, cell, test tube, etc. The antibody-adsorbed carrier should be stored at a cool place in the presence of appropriate preservatives, such as sodium azide.

Antibodies can be immobilized by known chemical binding or physical adsorption methods. Chemical binding methods include, for example, a method using glutaraldehyde, the maleimide method using N-succinimidyl-4-(N-maleimidomethyl) cyclohexane-1-carboxylate, N-succinimidyl-2-maleimidoacetate, etc., and the carbodiimide method using 1-ethyl-3-(3-dimethylaminopropyl) carbodiimide hydrochloride, etc. In addition, the maleimidobenzoyl-N-hydroxysuccinimidoester method, the N-succimidyl-3-(2-pyridyldithio)propionate method, the bisdiazolated benzidine method, and dipalmityllysine method. Alternatively, the complex produced by reacting two different antibodies against a substance to be detected and an epitope is captured with the third antibody immobilized by the above method.

Any label useful for immunoassay can be used without being limited. Specifically, enzymes, fluorescent substances, luminescent substances, radioactive substances, metal chelates, etc. can be used. Preferable labeling enzymes are, for example, peroxidase, alkaline phosphatase, β-D-galactosidase, malate dehydrogenase, Staphylococcus nuclease, delta-5-steroid isomerase, α-glycerol phosphate dehydrogenase, triosephosphate isomerase, horseradish peroxidase, asparaginase, glucose oxidase, ribonuclease, urease, catalase, glucose-6-phosphate dehydrogenase, glucoamylase, and acetylcholine esterase, etc. Preferable fluorescent substances include, for example, fluorescein isothiocyanate, phycobiliprotein, rhodamine, phycoerythrin, phycocyanin, allophycocyanin, and orthophthalaldehyde. Preferable luminescent substances include, for example, isoluminol, lucigenin, luminol, aromatic acridiniumester, imidazole, acridinium salt and its modified ester, luciferin, luciferase, and aequorine. Preferable radioactive substances include, for example, $^{125}I$, $^{127}I$, $^{131}I$, $^{14}C$, $^{3}H$, $^{32}P$, $^{35}S$, etc.

The method for binding the above labels is known. Specifically, direct and indirect labeling can be used. The common direct labeling is the method in which an antibody or an antibody fragment is chemically covalent-bound with a label using a crosslinking agent. Crosslinking agents include N,N'-orthophenylenedimaleimide, 4-(N-maleimidomethyl) cyclohexanoate N-succinimide ester, 6-maleimidohexanoate N-succinimide ester, 4,4'-dithiopyridine, and other known crosslinking agents. The crosslinking agent can be reacted with enzymes and antibodies by the known methods depending on the characteristics of the crosslinking agent. An example of the indirect labeling method comprises binding an antibody to a low molecular weight hapten such as biotin, dinitrophenyl, pyridoxal, or fluorescamine, and indirectly labeling the antibody with the binding partner to the hapten. Avidin and streptoavidin can be used as a recognition ligand for biotin, whereas dinitrophenyl, pyridoxal, or fluorescamine are labeled with antibodies recognizing these haptens. Horseradish peroxidase can be used as an enzyme for labeling antibodies. This enzyme is useful because it can react with many substrates and be easily bound to antibodies by the periodate method. Occasionally, as an antibody, their fragments, for example, Fab', Fab, F(ab')$_2$ are used. Both polyclonal and monoclonal antibodies can be labeled with an enzyme by the same method. Enzyme-labeled antibodies obtained using the above crosslinking agent can be purified by the known methods such as affinity chromatography, etc. to serve in a more sensitive immunoassay system. Purified enzyme-labeled antibodies are stored with a preservative such as thimerosal and a stabilizer such as glycerol. Labeled antibodies can be lyophilized and stored in the cool and dark place for a long time.

When a label is an enzyme, its substrate and, if necessary, a coloring agent are used for measuring its activity. When peroxidase is used as an enzyme, $H_2O_2$ is used as a substrate solution and 2,2'-azino-di-[3-ethylbenzothiazolinesulfonic acid] ammonium salt (ABTS), 5-aminosalicylic acid, orthtophenylenediamine, 4-aminoantipyrine, or 3,3', 5,5'-tetramethylbenzidine, etc. is used as a coloring agent. When alkaline phosphatase is used as an enzyme, orthonitrophenylphosphate, paranitrophenylphosphate, etc. can be used as substrates. When β-D-galactosidase is used as an enzyme, fluorescein-di-(β-D-galactopyranoside), 4-methylumbelliferyl-β-D-galactopyranoside, etc. can be used as substrates. The present invention also includes an immunoassay reagent for Meg-4, comprising labeled or immobilized monoclonal or polyclonal antibodies, and further includes a kit comprising this reagent and an indicator for detection label and a control sample, etc.

Any biological samples such as body fluid such as blood plasma, serum, blood, urine, tissue fluid, or cerebrospinal fluid etc. can be used as samples for measuring the Meg-4 of the present invention as long as they contain Meg-4 or its precursor or a fragment.

In addition, the present invention relates to a transgenic nonhuman vertebrate in which the expression level of Meg-4gene is altered. Herein, Meg-4 gene includes cDNA, genomic DNA, or synthetic DNA encoding Meg-4. Gene expression includes both steps of transcription and translation. Transgenic animals of the present invention are useful for investigating function and expression control of Meg-4, clarifying mechanisms of development of diseases relating to human mesangial cells, and developing disease model animals used for screening and testing safety of pharmaceuticals.

In the present invention, Meg-4 gene can be modified so as to artificially increase or decrease its expression level compared with the original gene by introducing mutation such as deletion, substitution, insertion, etc. in a part of some important sites (enhancer, promoter, intron, etc.) which control the normal expression of Meg-4 gene. Such modification alters transcription of Meg-4 gene. On the other hand, translation to proteins can be modified by deleting a part of an exon, or replacing a certain codon with a stop codon by introducing point mutation into coding regions. Such mutation can be introduced by the known methods for obtaining transgenic animals.

Transgenic animals means, in a narrow sense, animals into reproductive cells of which an exogenous gene is artificially introduced by genetic recombination, and in a broad sense, animals into chromosome of which an exogenous gene is stably introduced during an early developmental stage, the gene can be transmitted to the offspring as genotype, including antisense transgenic animals in which the function of a specific gene is inhibited by antisense RNA, animals in which a specific gene is knocked out by using embryonic stem cells (ES cells) and animals into which point mutation DNA is introduced. Transgenic animals used herein include all vertebrates except for human.

Transgenic animals can be prepared by the method comprising mixing a gene with an egg and treating the mixture with calcium phosphate, the microinjection method whereby a gene is directly injected into a nucleus in pronuclear egg by a micropipette under the phase contrast microscope (microinjection method, U.S. Pat. No. 4,873,191), and the method using embryo stem cells (ES cells). Other methods include, for example, the method in which a gene is inserted into a retrovirus vector to infect an egg and the sperm vector method in which a gene is introduced into an egg through sperm, etc. The sperm vector method is a genetic recombination method for introducing an exogenous gene by attaching an exogenous gene into sperm or incorporating an exogenous gene into sperm cells by electroporation, etc. and fertilizing an egg (M. Lavitranoet et al., Cell, 57, 717, 1989).

In vivo site-specific genetic recombination such as cre/loxP recombinase system of bacteriophage P1, FLP recombinase system of *Saccharomyces cerevisiae*, etc. can be used. The method for introducing a transgene of a target protein into nonhuman animals using retrovirus has been reported.

Transgenic animals can be prepared by micro injection, for example, in the following manner. A transgene basically composed of a promoter regulating expression, a gene encoding a specific protein, and poly (A) signal is provided. Expression pattern and level for all lineages should be confirmed since the expression pattern and level of a specific molecule depend on the promoter activity, and prepared transgenic animals vary among lineages depending on the number of copies and introduction site on chromosomes of an introduced transgene. A sequence of introns to be spliced at upstream of poly(A) signal may be introduced when the expression level is known to vary depending on noncoding region and splicing. It is important to use a gene as pure as possible for introducing into a fertilized egg. An animal to be used includes a mouse for collecting fertilized eggs (5 to 6 weeks old), male mouse for crossing, pseudopregnant female mouse, vasoligated male mouse, etc.

To efficiently obtain fertilized eggs, ovulation can be induced by gonadotropin, etc. A fertilized egg is collected, and a gene is injected into a male pronucleus of the egg by microinjection using an injection pipette. Animals for returning the treated eggs into an oviduct are prepared (pseudopregnant female mice, etc.), and about 10 to 15 eggs are transplanted per each individual. Introduction of the transgene into a new-born mouse is confirmed by extracting genomic DNA from the tip of the tail and detecting the transgene by Southern hybridization or PCR methods, or by the positive cloning method in which a marker gene that is activated only upon homologous recombination is inserted. Expression of the transgene can be confirmed by detecting a transgene-derived transcript by Northern hybridization or RT-PCR methods. Detection by Western blotting method is also possible using an antibody specific to a protein.

A knockout mouse of the present invention is prepared so as to lose the function of Meg-4 gene. A knockout mouse means a transgenic mouse in which a certain gene is destroyed by homologous recombination technology to eliminate its function. A knockout mouse can be prepared by conducting homologous recombination using ES cells and selecting ES cells in which one allele is modified and destroyed. For example, genetically manipulated ES cells are injected into a blastocyst or an 8-cell embryo of a fertilized egg to obtain a chimeric mouse having both cells derived from ES cells and from embryo. A heterozygous mouse in which all of one allele is modified and destroyed can be prepared by crossing a chimeric mouse (chimera means an individual composed of somatic cells derived from two or more fertilized eggs) and a normal mouse. Crossing of heterozygous mice with each other can produce homozygous mice. A transgenic animal of the present invention includes both heterozygotes and homozygotes.

Homologous recombination means the recombination occurring between two genes whose nucleotide sequences are the same or extremely similar through mechanism of genetic recombination. Cells with homologous recombination can be selected by PCR. Homologous recombination can be confirmed by performing PCR using as primers sequences of a part of a gene to be inserted and a part of a chromosomal region into which the gene is expectedly inserted and detecting cells producing amplified products. Homologous recombination in the genes expressed in ES cells can be easily screened by known methods or their modified methods, for example, by binding neomycin resistant gene to the introduced gene to make the cells neomycin resistant after the introduction.

BRIEF DESCRIPTION OF THE DRAWINGS

FIGS. 1A, 1B, 1C, and 1D shows a summary of the results of a motif search on Meg-4 by PSORT II (PSORT WWW Server, http://psort.nibb.ac.jp:8800/). The nucleotides of the DNA are indicated in such a manner so that the translation initiation position becomes 1. The nucleotide sequence and amino acid sequence are described in SEQ ID NO:1 and SEQ ID NO:2, respectively.

BEST MODE FOR CARRYING OUT THE INVENTION

Figure 2:
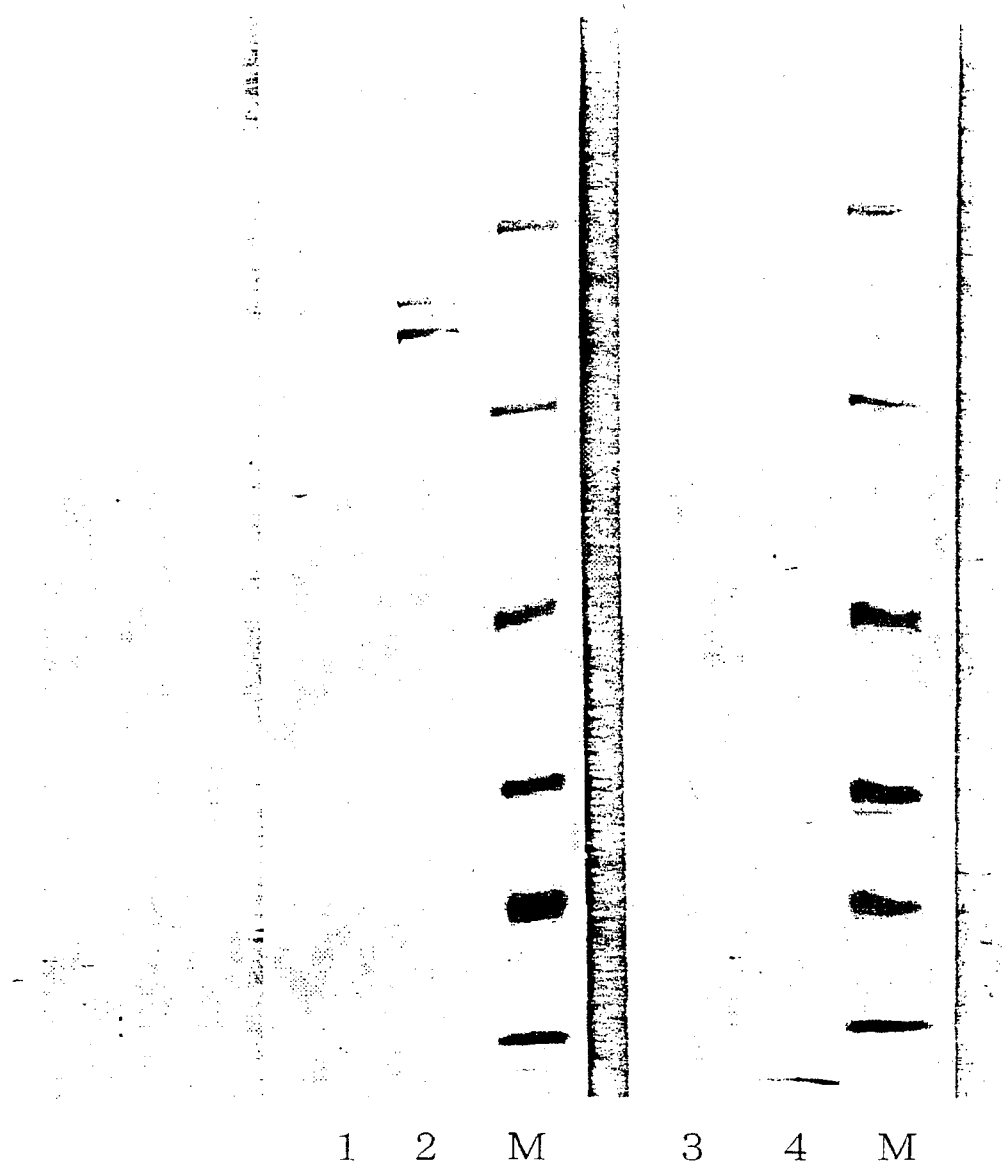
FIG. 2 is a photograph showing the results of a Western blot analysis with Meg-4 peptide antibody. Each lane corresponds to the following antigen. M indicates the molecular weight marker. Lane 1, Cell lysate of *E. coli* expressing MBP (anti-Meg-4 peptide IgG); Lane 2, Cell lysate of *E. coli* expressing MBP-Meg-4 (anti-Meg-4 peptide IgG); Lane 3, Cell lysate of expression *E.coli* (normal rabbit IgG); Lane 4, Cell lysate of *E. coli* expressing MBP-Meg-4 (normal rabbit IgG).

The present invention is illustrated in detail below with references to examples, but is not to be construed as being limited thereto.

EXAMPLE 1

Primary Culture of Human Mesangial Cells

Human glomerular renal mesangial cells were isolated from the normal human kidney excised from a 58 year-old male. Renal cortex was separated under the sterilized condition, minced, and passed through several sieves. Pore diameters of the used sieves were decreased stepwise, and the trapped glomerulus by the sieve at the pore diameter of 75 to 200 μm was washed and incubated with 100 μg/ml collagenase (Washington Biochemical) at 37° C. for 20 min. After washing, the glomerulus was resuspended in medium 199 (Gibco BRL, Gaithersburg, Md.) containing 25mMHepes, 10%Nu-serum (Collaborative Biomedical Products, Bedford, Mass.), and antibiotics (10 μg/ml of penicillin, streptomycin, and Fungizone), and incubated in the 5% $CO_2$ incubator. At the third passage, mesangial cells were identified based on a series of criteria such as typical morphological characteristics, resistance to trypsin, puromycin, and D-valine, positiveness against immunostaining of actin (ZymedLaboratories, SanFrancisco, Calif.), anti-very late antigen (VLA)-1, 3, 5 (Immunotech) andnegativeness against immunostaining of VIII factor (Dako, Calif.)

EXAMPLE 2

Isolation of mRNA from Human Cultured Mesangial Cells

At the sixth passage, total RNA was isolated from human mesangial cells using guanidine isothiocyanate (GTC) method. The confluent culture of the mesangial cells in the medium containing serum of the cells of Example 1 was washed with phosphate buffer saline (PBS), and dissolved in 5.5 mM GTC solution. DNA was removed by passing through an 18-gauge needle. Nuclei and other cell debris were precipitated by centrifugation at 5,000×g for 90 sec. Supernatant was carefully loaded on the layer of cesium trifluoroacetate (CsTFA) and centrifuged at 125,000×g at 15° C. for 24 hours. RNA pellet was dissolved in TE buffer. Poly(A)$^+$ RNA was isolated using oligo dT cellulose column (Pharmacia).

EXAMPLE 3

Construction of 3'-Directed cDNA Library cDNA was synthesized using the vector primer based on pUC19 (Norrander J. et al., Gene, 26, 101–106, 1983) with poly(A)$^+$ RNA as a template. This vector primer DNA comprised the HincII end and the PstI end with a T tale, and dam-methylated at the MboI site (GATC). After synthesizing the second strand, the cDNA sequence and the single BamHI site in LacZ gene of the vector were digested with MboI and BamHI, respectively, and circularizion and ligation were conducted at the low DNA concentration. A portion of the ligation mixture was transformed to *E. coli*. The obtained transformants were randomly selected and individually dissolved by simply heating. The inserted sequence of cDNA was amplified by the paired PCR using primers (5'-TGTAAAACGACGGCCAGT-3'/SEQ ID NO: 3 and 5'-ACCATGATTACGCCAAGCTTG-3'/SEQ ID NO: 4) flanking the pUC19 cloning site. The obtained short double stranded DNA was used for the cycle sequence determination reaction and analyzed by anautomatic sequencer.

EXAMPLE 4

Isolation of Genes Expressed Specifically in Mesangial Cells

In order to identify genes expressed specifically in mesangial cells, the present inventor conducted large scale DNA sequencing and data processing by computers. Transcripts in the various different cells and organs could be simultaneously compared (Y. Yasuda et al., Kidney International 53:154–158, 1998; K. Matsubara et al., Gene. 135, 265 (1993); K. Okubo et al., Nat. Gen. 2, 173 (1992)). Large scale DNA sequencing of the 3'-domain cDNA library of human cultured mesangial cells was conducted, and randomly selected 1836 clones were sequenced for their partial sequences. The sequence homology among clones was mutually compared, and further compared with that in DNA data bank GenBank using FASTA program. mRNA from various organs and cells were analyzed using dot blot to select clones expressed specifically in mesangial cells. As a result, some clones detected at extremely high frequency in the mesangial cell cDNA library were obtained.

EXAMPLE 5

Screening of Human Mesangial Cell λZIPLox cDNA Library

From the complete mRNA prepared according to Example 2, the λZIPLox cDNA library was synthesized using oligo (dT) primer and random primer. Commercially available λZIPLox (Gibco BRL, λZIPLox EcoRI Arms) was used to synthesize this library. This λZIPLox cDNA library was screened for a specific clone that was detected particularly frequently in the mesangial cell cDNA library, obtained in Example 4, by using its insert as a probe. The nucleotide sequence of the inserted gene segment was determined for the positive clone (2 clones) by the dideoxy termination method.

Sequence determination results showed that one of the two isolated clones included a portion of ORF and 3'

UTR-poly(A) and that the other included a portion of ORF and 5' UTR. The two nucleotide sequences have overlapping regions, and through alignment, the nucleotide sequence of SEQ ID NO: 1 was determined to be the cDNA nucleotide sequence. In this cDNA nucleotide sequence, 773 amino acid residues based on the longest ORF was estimated to be the deduced amino acid sequence of the gene product. The protein with this amino acid sequence was named Meg-4 by the present inventor.

EXAMPLE 6

Functional Analysis of a Mesangium-Specific Gene (1)

An amino acid homology search performed by the program FASTA using the SwissProt database confirmed that this Meg-4 protein is a novel protein. Mouse ATP-MP was identified as a homologous protein. Meg-4 and ATP-MP has 89.8% amino acid sequence homology and 81.7% cDNA nucleotide sequence homology. In addition, in Meg-4, 58 amino acid residues (56–115) were inserted to the position corresponding to amino acid positions 55–58 of ATP-MP. ATP-MP was speculated to be a homologue of Meg-4 in mouse.

Next, amotif search was carried out on the Meg-4 amino acid sequence PSORTWWWServer (http://psort.nibb.ac.jp:8800/) was used for the search. The search results are summarized in FIG. 1. As FIG. 1 shows, it was demonstrated that Meg-4 includes a motif of the AAA protein family (Patel, S., Latterich, M., Trends in Cell Biol., 1998, 8: 65–71). Specifically, the existence of motifs common to the AAA protein family was confirmed in the following positions.

379–386: ATP binding motif
476–494: minimum AAA protein motif
434–438: walker B motif
600–603: Zn binding motif In addition, based on these facts, it was confirmed that the deduced amino acid sequence mentioned above was the Meg-4 amino acid sequence.

The AAA motif characteristic of the AAA protein is a conserved amino acid sequence in many species such as plants, bacteria, and mammals. For this reason, it is speculated that the AAA protein family are proteins that have the important functions of supporting basic cellular functions. Therefore, the fact that Meg-4, having the characteristics such as those mentioned above, is highly expressed in mesangial cells suggests that this protein has an important role in maintaining the form and function of renal cells.

Meanwhile, several proteases are produced in the renal mesangial cells, and these are thought to be partly responsible for cellular function. Judging from the characteristics of its gene structure, there is a possibility that Meg-4 has protease activity. This also indicates that Meg-4 may be deeply involved in the physiology of the renal mesangial cells and the physiology of diseased conditions.

Although mitochondrial metalloprotease (Casari G. et al., Cell, 1998, 93: 973–983) is reported in humans as an example of the AAA protein, there is almost no homology to Meg-4 except for the AAA protein motif. FtsH originating from prokaryotic cells (E. coli) (Santos and Almeida, J. Bacteriol. 1975, 124: 1502–1507) and YME1 (Thorsness, P. E., Mol. Cell Biol. 1993, 5418–5426) isolated from yeast (S. cerevisiae) are also reported to be AAA proteins. Meg-4 may be considered one of the homologues of these proteins in humans. However, besides the AAA motif, amino acid sequence homology cannot be found with any of these proteins.

EXAMPLE 7

Functional Analysis of Meg-4 (2)-Tissue Distribution

Northern blot analysis of Meg-4 was performed as described in the following. The positive clone insert of the 3' directed cDNA library (Example 3) was labeled with RI by random DNA labeling and was used as a probe. Poly(A)$^+$ (2 μg) isolated from the below-mentioned cells to be used as samples was separated on a 1% agarose gel containing 2.2 M formamide and was transferred onto a nitrocellulose filter. The filter was hybridized in Rapid Hyb solution (Amersham, Arlington Heights, Ill.). After hybridization, it was washed with final stringency of 0.1×SSPE/0.1% SDS at 60° C.

Samples for Northern blot analyses of multiple human primary culture cells and tissues, and for Northern blot analysis of human cancer cell lines were purchased from Clontech (Palo Alto, Calif.). As samples of primary culture cells, 2 μg of poly (A)$^+$ from primary culture cells of mesangial cells, human dermal epithelial cells, human renal cortical epithelial cells, human endothelial cells of the umbilical vein, and human smooth muscle cells were used. For Northern blot analysis of human cancer cell lines, 2 μg of poly (A)$^+$ RNA derived from promyelocytic leukemia HL-60, HeLa cells S3, chronic myeloid leukemia K-562, lymphoblastic leukemia MOLT-4, Burkitt's lymphoma Raji, adenocarcinoma of the large intestine SW480, lung cancer A549, and melanoma G361were used as samples. For Northern blot analysis of the tissues, 2 μg of poly(A)$^+$ derived from the heart, brain, placenta, lung, liver, skeletal muscles, kidney and pancreas were used as samples. Hybridization and washing were carried out as described above. The results are as indicated in Tables 1–3.

TABLE 1

| primary culture cells | |
| --- | --- |
| mesangial cells | + + + |
| human dermal epithelial cells | + + |
| human renal cortical epithelial cells | + |
| human endothelial cells of the umbilical vein | ± |
| human smooth muscle cells | ± |

TABLE 2

| human cancer cell lines | |
| --- | --- |
| promyelocytic leukemia HL-60 | ± |
| HeLa cells S3 | + |
| Chronic myeloid leukemia K-562 | + |
| lympphoblastic leukemia MOLT-4 | ± |
| Burkitt's lymphoma Raji | – |
| adenocarcinoma of the large intestine SW480 | + |
| lung cancer A549 | + |
| melanoma G361 | – |

TABLE 3

| human tissues | |
| --- | --- |
| Heart | + |
| Brain | + |
| placenta | + |
| Lungs | ± |
| Liver | ± |
| skeletal muscle | + + |
| Kidney | + |
| pancreas | + |

In the Northern blot analysis using Meg-4 cDNA as a probe, a single transcription product (approximately 4 kb)

was found in the cultured mesangial cells. Comparing the tissues, expression was observed in tissues such as human kidney, heart, brain, placenta, skeletal muscles and pancreas, expression was weak in the lung and liver, but especially high levels of expression was confirmed in the mesangial cells. Noticeable expression was not observed in cultured cancer cell lines.

EXAMPLE 8

Analysis of the Meg-4 Phenotype

Example 6 pointed out the possibility that Meg-4 protein of this invention is the human homologue of E. coli FtsH and yeast YME1L, which are reported to be AAA proteins. However, the amino acid sequence (AF070656) reported after submission of this application, as the human counterpart of FtsH, was found to start from Met at position 225 of Meg-4. Furthermore, the translation frame was shifted in the 3'-end. Also, compared to the sse-PV-lnlr region corresponding to positions 55–58 in the amino acid sequence of mouse FtsH, which was reported after submission of this application, Meg-4 of this invention showed insertion and replacement of 59 amino acids, sse-(59 aa insertion and replacement)-lnlr. Based on such information, isolation of the phenotype of Meg-4 in humans was attempted.

That is, the human mesangial cell λZIPLox cDNA library obtained in Example 5 was used as a template to amplify the cDNA by PCR method using the following primer set. This primer set is designed to amplify the nucleotide sequence encoding positions 56 to 116 of the Meg-4 amino acid sequence (SEQ ID NO: 2).

Sense primer (5'-end) 5'-atgttttcct tgtcgagcac ggtgcaaccc c-3'/SEQ ID NO: 5

Antisense primer (AS754) 5'-tctcggaggt agactggaga cgtcgtgtcc t-3'/SEQ ID NO: 6

As a result, the existence of cDNA made of the nucleotide sequence of SEQ ID NO: 7 in the obtained amplified product was confirmed. The deduced amino acid sequence encoded by this nucleotide sequence is indicated in SEQ ID NO: 8. In the amino acid sequence of SEQ ID NO: 8, the amino acid sequence corresponding to the region of positions 56 to 116 of Meg-4 was sse-PS-lnlr. Furthermore, the amino acid sequence (AJ132637) of human YME1L (Homo sapiens mRNA for ATP-dependent metalloprotease YME1L.) reported after submission of this application has 98.3% sequence homology to Meg-4 indicated in SEQ ID NO: 2 and the amino acid sequence corresponding to position 55 to 58 of SEQ ID NO: 8 was shown to be sse-PS-lnlr. Summarizing these findings, the relationship among this series of amino acid sequences can be shown as follows.

| SEQ ID NO: 2 (Meg-4) | sse- | ... 59aa ... | -lnlr |
|---|---|---|---|
| mouse FtsH | sse- | PV | -lnlr |
| SEQ ID NO: 8 (Meg-4 phenotype) | sse- | PS | -lnlr |
| human YME1L(AJ132637) | sse- | PS | -lnlr |

From the above, human Meg-4 of this invention is presumed to have functions similar to that of YME1L.

EXAMPLE 9

Production of Polyclonal Antibodies Against Synthetic Peptides of Meg-4

A region that has low homology to other AAA family proteins and has hydrophilicity was used as an antigen to produce polyclonal antibodies against Meg-4. Apeptide that has cysteine at its N-terminal or C-terminal and has the amino acid sequence indicated below was prepared by solid phase peptide synthesis. Position from the N-terminal Amino acid sequence 574–593 KDKILMGPERRSVEIDNKNK(SEQ ID NO: 9)

Each of the synthesized peptides and adjuvant (Difco) were thoroughly mixed, emulsified, and administered to rabbit, subcutaneously. Upon priming (20 µg/individual), 4 additional immunizations were carried out 3 weeks after priming (50 µg/individual) and every two weeks thereafter (50, 100, 200µg/individual). Withregard to the adjuvant, initially Freund's complete adjuvant was used, and from the second immunization and thereafter, Freund's incomplete adjuvant was used. In order to confirm that the sera obtained from blood collected after 41 and 55 days reacts with the synthetic peptides, the antibody titer of the sera was evaluated by enzyme-linked immunosorbent assay (ELISA). To a 96-well plate coated with 50 ng/well of antigen, 100 µL of successively diluted antisera was added to each of the wells to perform the primary reaction, and upon washing, HRP-conjugated goat anti-rabbit IgG (Cappel Product) was reacted as a secondary reaction. After washing, o-phenylenediamine (Wako Pure Chemical Industries) was added as substrate for coloring, and absorbance measurement at 492 nm confirmed the increase in antibody titer.

EXAMPLE 10

Purification Method of Polyclonal Antibodies Against Synthetic Peptides of Meg-4

Polyclonal antibodies against synthetic peptides of Meg-4 was purified by affinity chromatography following known methods (Saibou Kougaku Bessatsu (Cell Biotechnology Supplementary Volume) Experimental Protocol Series, Anti-Peptide Experiment Protocol, Shujun-sha). The protocol is the following.

Purification of PBS(−) diluted rabbit sera, which had elevated antibody titer due to Meg-4 immunization, was accomplished by affinity chromatography on a protein G column for IgG purification. The obtained purified antibody was checked for reaction with Meg-4 protein-conjugated protein by Western blot analysis to prove that it is specific to Meg-4 (Example 11).

EXAMPLE 11

Reactivity Examination of Rabbit Polyclonal Anti-Meg-4 Peptide IgG

Using, as antigens, MBP-Meg-4 and lysate of E. coli expressing MBP alone, the reactivity of rabbit IgG whose immunogen was the Meg-4 peptide was confirmed. MBP-Meg-4 was prepared as follows. The coding region was amplified by PCR based on the nucleotide sequence of the MEGSIN gene indicated in SEQ ID NO: 1. Insertion of this amplified product into the maltose binding protein-conjugated protein expression vector, pMAL-c (New England Biolab), yielded a vector expressing a conjugated protein formed between MBP and the MEGSIN protein. E. coli was transformed with this vector, and its cell lysate was used as MBP-Meg-4.

Samples were obtained by treating each of the protein solutions with the same amount of sample buffer (0.25% Tris-HCl, 2% SDS, 30% glycerine, 10% β-mercaptoethenol, 0.025% bromophenol blue) (Daiichi Chemicals) and heating them at 100° C. for 5 minutes. The obtained samples were separated by SDS-polyacrylamide gel electrophoresis (SDS-PAGE) (Laemmli, U. K., Nature, 1970, 227: 680–685) using a gradient gel with gel concentration of 4–20% (Daiichi Chemicals).

Proteins separated by SDS-PAGE were blotted onto a polyvinylidene difluoride (PVDF) membrane (BioRad) by treatment in a blotting solution (25 mM Tris-HCl, 192 mM glycine, 20% methanol, pH8.3) for 1 hour at constant voltage of 100 V. After washing the blotted PVDF membrane with distilled water, it was blocked in a 5% Block Ace solution in TTBS for 3 hours. Next, after washing the PVDF membrane with TTBS (20 mM Tris, 500 mM NaCl, 0.05% Tween 20, pH7.5) it was reacted overnight at 4° C. with a solution of rabbit polyclonal anti-Meg-4 peptide IgG which is a primary antibody diluted with TTBS. Next, detection was carried out using Amplified Alkaline Phosphatase Immune Blot Kit. (Biorad). In other words, after 1-hour incubation at room temperature with biotin-labeled goat anti-rabbit IgG diluted with TTBS, it was reacted with a previously prepared complex of streptavidin-biotin-labeled alkaline phosphatase for 1 hour by incubating streptavedin-biotin-labeled alkaline phosphatase at room temperature. By washing the PVDF membrane with TTBS and incubating it with a substrate (nitro blue tetrazolium and 5-bromo-4-chloro-3-indolyl phosphate, p-toluidine salt solution) at room temperature for approximately 30 minutes, the antibody bound to the primary antibody was visualized. The reaction was terminated by thorough reaction with distilled water.

The results are shown in FIG. 2. The band corresponding to MBP-Meg-4 was confirmed using the polyclonal anti-Meg-4 antibody of this invention obtained through Example 10. Therefore, it was shown that this polyclonal antibody was an antibody that specifically recognizes Meg-4.

EXAMPLE 12

Analysis of the Localization of the Meg-4 Gene on the Chromosome using the FISH Method The DNA of clone F960 was labeled with digoxigenin dUTP by the nick translation method. Clone F960 is a positive clone obtained by screening the human genome Bac (bacterial artificial chromosome) library using a Meg-4 specific probe. The Meg-4 specific probe used for Bac library screening is a segment that corresponds to the Kpn-I/Sca I digestion fragment of ZIPLox cDNA clone, which contains the 5' region (0–644 nt) of cDNA as an insert.

The labeled probe was treated with digested human DNA and subsequently hybridized with a normal metaphase human chromosome. The human chromosome was obtained by treating a peripheral blood lymphocyte stimulated with PHA in a solution containing 50% formamide, 10% dextransulfate, and 2xSSC. The hybridization signal was detected by a counterstain with DAPI, followed by reaction with a fluorescein-bound anti-digoxigenin antibody.

Figure 3:
FIG. 3 is a fluorescence micrograph showing the results of chromosome analysis by FISH method using Meg-4 cDNA as a probe. Those indicated by white arrows are signals detected by Meg-4 cDNA.
Figure 4:
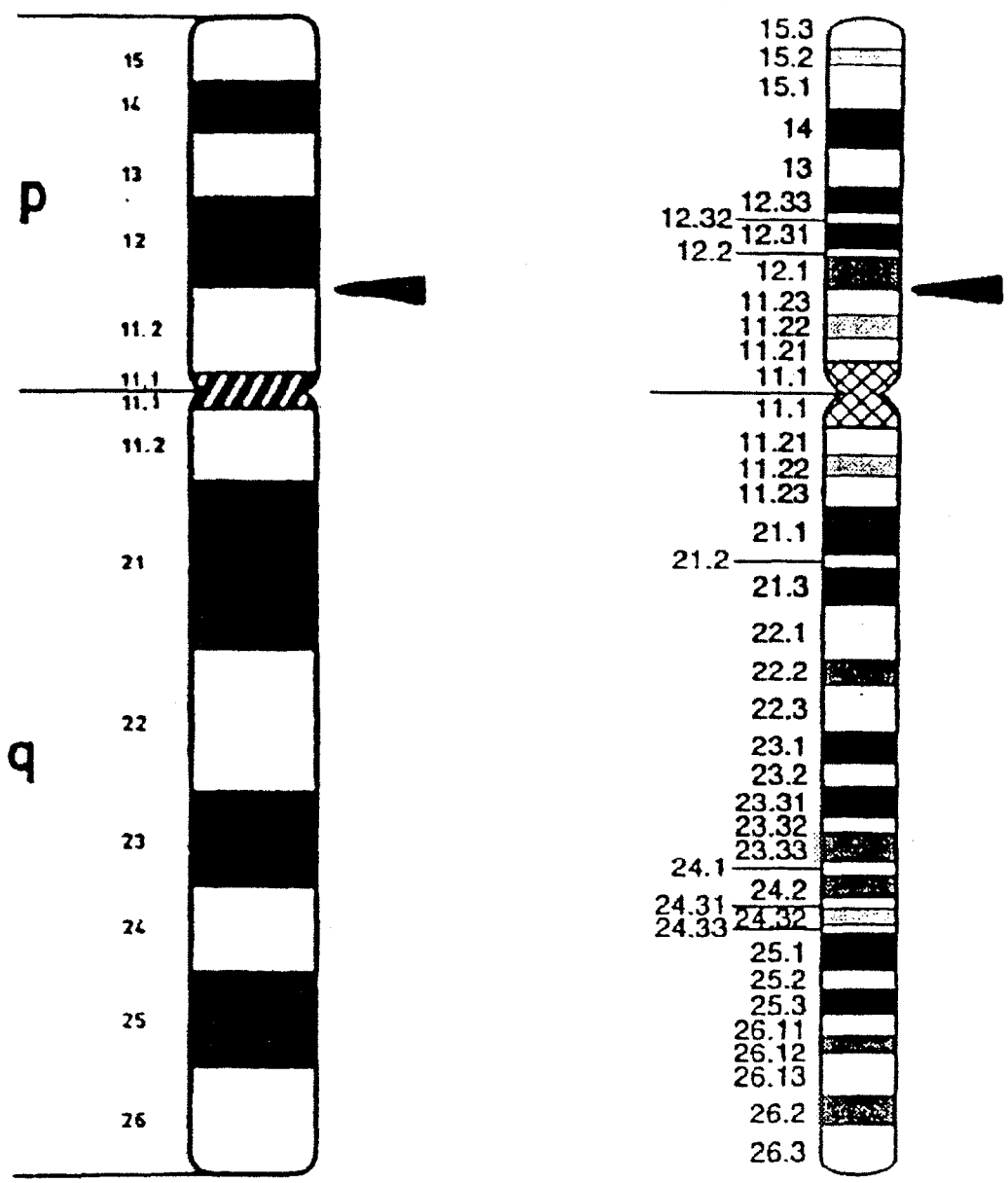
FIG. 4 is an idiogram indicating the 10p11.23–12.1. position, where the Meg-4 gene is localized. All of the idiograms are based on the international nomenclature.

From this experiment, a characteristic signal was observed in the short arm of group C chromosome, which is thought to be chromosome 10, based on its size, characteristic form and band pattern (FIG. 3).

Next, the anonymous probe mapped on. 10q22 (long arm), centromere-specific probe of chromosome 10, and clone F960 were co-stained. This experiment allows the comparison of signals specific to the long arm and the short arm. According to the analysis that uses probe 10, which is specific to chromosome 10, F960 was mapped at a distance of 23% with respect to the region from the centromere to the telomere of chromosome 10p. This region corresponds to 10p11.23–12.1. Among the 80 metaphse cells that were analyzed, 75 showed signals specific to F960.

Industrial Applicability

The present invention provides a DNA expressed at high frequency inmesangial cells, a protein encoded by the DNA, and an antibody binding to the protein, etc. These are supposed to be closely related to mesangial cell-specific bioactivity, and useful for, for example, identifying mesangial cells, and detecting abnormalities in mesangial cells. Moreover, this protein would be helpful for clarifying the functions of mesangial cells and in turn, for investigating causes of diseases relating to mesangial cells. This invention is expectedly applicable to the treatment and diagnosis, and such of diseases relating to mesangial cells.

Specifically, the onset or progress of glomerulonephritis may be regulated, for example, by artificially adjusting Meg-4. Alternatively, quantification of mRNA and protein of Meg-4 in the body fluid and mesangial cells may enable diagnosis of renal diseases such as glomerulonephritis. In glomerulonephritis, functional abnormality is seen in the mesangium region, causing proliferation of mesangial cells or acceleration of matrix production from the cells. The possibility that Meg-4 is involved in these diseases is great.

Meg-4 of this invention and MEGSIN, which was previously reported by the present inventor, share common characteristics with regard to high levels of expression in the mesangial cells. However, Meg-4 of this invention is thought to belong to the ATP-MP group of the AAA protein family, whereas MEGSIN is a protein that is homologous to the SERPIN superfamily, which is a protease inhibitor. In addition, the observation that Meg-4 of this invention is expressed in a variety of tissues is different from the characteristic of MEGSIN, which is expressed specifically in mesangial cells. Therefore, Meg-4 of this invention may possibly be an important protein that supports the function of mesangial cells. This invention, which has elucidated the existence of such an important protein, has great significance.

What is claimed is:

1. An isolated protein comprising an amino acid sequence that has ATPase activity and not less than a 90% homology with the amino acid sequence of SEQ ID NO:2.

2. The isolated protein comprising an amino acid sequence of SEQ ID NO.:2.

* * * * *

SEQUENCE LISTING

<160> NUMBER OF SEQ ID NOS: 9

<210> SEQ ID NO 1
<211> LENGTH: 3941
<212> TYPE: DNA
<213> ORGANISM: Homo sapiens

<400> SEQUENCE: 1

```
ctatagggaa agctggtacg cctgcaggta ccggtccgga aattcgcggc cgcgtcgacg      60
ggtgaggtcg ctgagggccc gccgggggtg aggtcgctga gggcccgccg gagatgtttt     120
ccttgtcgag cacggtgcaa ccccagttta cagttcctct gagtcatctc atcaatgcct     180
tccatacacc aaaaaacact tctgtttctc tcagtggagt gtcagtttct caaaaccagc     240
atcgagatgt agttcctgag catgaggctc ccagcagtga gtgtatgttc agtgacttcc     300
tgacgaagct taacattgtt tcaatcggca aaggaaaaat attcgaaggg tacagatcca     360
tgttcatgga gccagcaaaa aggatgaaga agagcttgga cacaaccgat aactggcaca     420
tccgtccaga acccttctcc ctctcaatcc ctccttcact taacttaagg gaccttggat     480
tatctgaatt aaaaattgga cagattgatc agctggtaga aaatctactt cctggatttt     540
gtaaaggcaa aaacatttct tcccattggc atacatccca tgtctctgca caatccttct     600
ttgaaaataa atatggtaac ttagatatat ttagtacatt acgttcctct tgcttgtatc     660
gacatcattc aagagctctt caaagcattt gttcagatct tcagtactgg ccagttttca     720
tacagtctcg gggttttaaa actttgaaat caaggacacg acgtctccag tctacctccg     780
agagattagc tgaaacacag aatatagcgc catcattcgt gaaggggttt cttttgcggg     840
acagaggatc agatgttgag agtttggaca aactcatgaa aaccaaaaat atacctgaag     900
ctcaccaaga tgcatttaaa actggttttg cggaaggttt tctgaaagct caagcactca     960
cacaaaaaac caatgattcc ctaaggcgaa cccgtctgat tctcttcgtt ctgctgctat    1020
tcggcatttta tggacttcta aaaaacccat ttttatctgt ccgcttccgg acaacaacag    1080
ggcttgattc tgcagtagat cctgtccaga tgaaaaatgt caccttttgaa catgttaaag    1140
gggtggagga agctaaacaa gaattacagg aagttgttga attcttgaaa aatccacaaa    1200
aatttactat tcttggaggt aaacttccaa aaggaattct tttagttgga cccccaggga    1260
ctggaaagac acttcttgcc cgagctgtgg cgggagaagc tgatgttcct ttttattatg    1320
cttctggatc cgaatttgat gagatgtttg tgggtgtggg agccagccgt atcagaaatc    1380
tttttaggga agcaaaggcg aatgctcctt gtgttatatt tattgatgaa ttagattctg    1440
ttggtgggaa gagaattgaa tctccaatgc atccatattc aaggcagacc ataaatcaac    1500
ttcttgctga aatggatggt tttaaaccca atgaaggagt tatcataata ggagccacaa    1560
acttcccaga ggcattagat aatgccttaa tacgtcctgg tcgttttgac atgcaagtta    1620
cagttccaag gccagatgta aaaggtcgaa cagaaattttt gaaatggtat ctcratanaw    1680
taaagtttga tcaatccgtt gatccagaaa ttatagctcg aggtactgtt ggcttttccg    1740
gagcagagtt ggagaatctt gtgaaccarg ctgcattaaa agcagctgtt gatggaaaag    1800
aaatggttac catgaaggag ctggagtttt ccaaagacaa aattctaatg gggcctgaaa    1860
gaagaagtgt ggaaattgat aacaaaaaca aaccatcac agcatatcat gaatctggtc    1920
atgccattat tgcatattac acaaaagatg caatgcctat caacaaagct acaatcatgc    1980
cacggggggcc aacgcttgga catgtgtccc tgttacctga aatgacaga tggaatgaaa    2040
ctagagccca gctgcttgca caaatggatg ttagtatggg aggaagagtg gcagaggagc    2100
ttatatttgg aaccgaccat attacaacag gtgcttccag tgattttgat aatgccacta    2160
aaatagcaaa gcgatggtt accaaatttg gaatgagtga aaagcttgga gttatgacct    2220
acagtgatac agggaaacta agtccagaaa cccaatctgc catcgaacaa gaaataagaa    2280
```

-continued

```
tccttctaag ggactcatat gaacgagcaa acatatcttt gaaaactcat gcaaaggagc   2340
ataagaatct cgcagaagct ttattgacct atgagacttt ggatgccaaa gagattcaaa   2400
ttgttcttga ggggaaaaag ttggaagtga atgataact ctcttgatat ggatgcttgc    2460
tggttttatt gcaagaatat aagtagcatt gcagtagtct acttttacaa cgctttcccc   2520
tcattcttga tgtagtgtaa ttgaagggtg tgaaatgctt tgtcaatcat ttgtcacatt   2580
tatccagttt gggttattct cattatgaca cctattgcaa attagcatcc catggcaaat   2640
atattttgaa aaataaaga actatcagga ttgaaaacag ctcttttgag gaatgtcaat    2700
tagttattaa gttgaaagta attaatgatt ttatgtttgg ttactctact agatttgata   2760
aaaattgtgc ctttagcctt ctatatacat cagtggaaac ttaagatgca gtaattatgt   2820
tccagattga ccatgaataa aatatttttt aatctaaatg tagagaagtt gggattaaaa   2880
gcagcctcgg aaacacagag ccaggaatat agccttttgg catggtgcca tggctcacat   2940
ctgtaatccc agcacttttg gaggctgagg cgggtggatt gcttgaggcc aggagttcga   3000
gaccagcctg gccaacgtgg tgaaacgctc tctctactaa aatacaaaaa aatagggctg   3060
ggcgcggttg ctcacgcctg taatcccagc acttttcaga ggccaaggcg ggcaaatcac   3120
ctgaggtcaa gagtttgaga ccagcctggc caacatggtg aaacccatc tctactaaac   3180 atgcaaaaat tacctgggca tggtggcagg tgcttataat cccagctact ctgggggcca   3240
aggcaggaga attgcttgag cctgggagat ggaggttgca gtgagctgag atcatgccac   3300
tgcactccag cctgggcaac agagcaagac tctgcctcaa aaaaaatta aataaattt    3360 aaatacaaaa aaaatagcc aggtgtgggg tgcatgcctg gaatcccagc tacttgagag    3420
gctgaggcac gagaattgct tgaacccagg aggtggaggt tgcagtgagc caagatcaca   3480
ggagccactg cactccagcc tgggtgacag agtgagactc tgtctcaaaa aaaaaattaa   3540
ataaattatt ataacctttc agaaatgctg tgtgcatttt catgttcttt tttttagcat   3600
tactgtcact ctccctaatg aaatgtactt cagagaagca gtattttgtt aaataaatac   3660
ataacctcat tctgaataat gtccctcatt ttgactataa ctgtgcttgg tttcaaaagc   3720
aaaattaaac aaaaatctca gtcccctccg aagtgaactt tgtgttaccc tgcgtcagaa   3780
atgccaagtt gtgtttactt ttcattcaga ttttgtgaat atgaacatgc tgttatagga   3840
tctacagatg aatatttaac tcaatagaaa aattatttta gaacacattg tattggtatt   3900
tacaaccaga ttatattctt gacgttgact tcattaaaat t                      3941
```

<210> SEQ ID NO 2
<211> LENGTH: 773
<212> TYPE: PRT
<213> ORGANISM: Homo sapiens
<220> FEATURE:
<221> NAME/KEY: VARIANT
<222> LOCATION: 523
<223> OTHER INFORMATION: Xaa = Any Amino Acid
<220> FEATURE:
<221> NAME/KEY: VARIANT
<222> LOCATION: 523
<223> OTHER INFORMATION: Xaa = Any Amino Acid

<400> SEQUENCE: 2

```
Met Phe Ser Leu Ser Ser Thr Val Gln Pro Gln Phe Thr Val Pro Leu
 1               5                  10                  15

Ser His Leu Ile Asn Ala Phe His Thr Pro Lys Asn Thr Ser Val Ser
            20                  25                  30

Leu Ser Gly Val Ser Val Ser Gln Asn Gln His Arg Asp Val Val Pro
```

-continued

```
            35                  40                  45
Glu His Glu Ala Pro Ser Ser Glu Cys Met Phe Ser Asp Phe Leu Thr
 50                  55                  60
Lys Leu Asn Ile Val Ser Ile Gly Lys Gly Lys Ile Phe Glu Gly Tyr
 65                  70                  75                  80
Arg Ser Met Phe Met Glu Pro Ala Lys Arg Met Lys Lys Ser Leu Asp
                 85                  90                  95
Thr Thr Asp Asn Trp His Ile Arg Pro Glu Pro Phe Ser Leu Ser Ile
                100                 105                 110
Pro Pro Ser Leu Asn Leu Arg Asp Leu Gly Leu Ser Glu Leu Lys Ile
                115                 120                 125
Gly Gln Ile Asp Gln Leu Val Glu Asn Leu Leu Pro Gly Phe Cys Lys
130                 135                 140
Gly Lys Asn Ile Ser Ser His Trp His Thr Ser His Val Ser Ala Gln
145                 150                 155                 160
Ser Phe Phe Glu Asn Lys Tyr Gly Asn Leu Asp Ile Phe Ser Thr Leu
                165                 170                 175
Arg Ser Ser Cys Leu Tyr Arg His His Ser Arg Ala Leu Gln Ser Ile
                180                 185                 190
Cys Ser Asp Leu Gln Tyr Trp Pro Val Phe Ile Gln Ser Arg Gly Phe
                195                 200                 205
Lys Thr Leu Lys Ser Arg Thr Arg Leu Gln Ser Thr Ser Glu Arg
                210                 215                 220
Leu Ala Glu Thr Gln Asn Ile Ala Pro Ser Phe Val Lys Gly Phe Leu
225                 230                 235                 240
Leu Arg Asp Arg Gly Ser Asp Val Glu Ser Leu Asp Lys Leu Met Lys
                245                 250                 255
Thr Lys Asn Ile Pro Glu Ala His Gln Asp Ala Phe Lys Thr Gly Phe
                260                 265                 270
Ala Glu Gly Phe Leu Lys Ala Gln Ala Leu Thr Gln Lys Thr Asn Asp
                275                 280                 285
Ser Leu Arg Arg Thr Arg Leu Ile Leu Phe Val Leu Leu Phe Gly
                290                 295                 300
Ile Tyr Gly Leu Leu Lys Asn Pro Phe Leu Ser Val Arg Phe Arg Thr
305                 310                 315                 320
Thr Thr Gly Leu Asp Ser Ala Val Asp Pro Val Gln Met Lys Asn Val
                325                 330                 335
Thr Phe Glu His Val Lys Gly Val Glu Glu Ala Lys Gln Glu Leu Gln
                340                 345                 350
Glu Val Val Glu Phe Leu Lys Asn Pro Gln Lys Phe Thr Ile Leu Gly
                355                 360                 365
Gly Lys Leu Pro Lys Gly Ile Leu Leu Val Gly Pro Pro Gly Thr Gly
                370                 375                 380
Lys Thr Leu Leu Ala Arg Ala Val Ala Gly Glu Ala Asp Val Pro Phe
385                 390                 395                 400
Tyr Tyr Ala Ser Gly Ser Glu Phe Asp Glu Met Phe Val Gly Val Gly
                405                 410                 415
Ala Ser Arg Ile Arg Asn Leu Phe Arg Glu Ala Lys Ala Asn Ala Pro
                420                 425                 430
Cys Val Ile Phe Ile Asp Glu Leu Asp Ser Val Gly Gly Lys Arg Ile
                435                 440                 445
Glu Ser Pro Met His Pro Tyr Ser Arg Gln Thr Ile Asn Gln Leu Leu
450                 455                 460
```

```
Ala Glu Met Asp Gly Phe Lys Pro Asn Glu Gly Val Ile Ile Ile Gly
465                 470                 475                 480

Ala Thr Asn Phe Pro Glu Ala Leu Asp Asn Ala Leu Ile Arg Pro Gly
                485                 490                 495

Arg Phe Asp Met Gln Val Thr Val Pro Arg Pro Asp Val Lys Gly Arg
            500                 505                 510

Thr Glu Ile Leu Lys Trp Tyr Leu Asx Lys Xaa Lys Phe Asp Gln Ser
        515                 520                 525

Val Asp Pro Glu Ile Ile Ala Arg Gly Thr Val Gly Phe Ser Gly Ala
    530                 535                 540

Glu Leu Glu Asn Leu Val Asn Gln Ala Ala Leu Lys Ala Ala Val Asp
545                 550                 555                 560

Gly Lys Glu Met Val Thr Met Lys Glu Leu Glu Phe Ser Lys Asp Lys
                565                 570                 575

Ile Leu Met Gly Pro Glu Arg Arg Ser Val Glu Ile Asp Asn Lys Asn
                580                 585                 590

Lys Thr Ile Thr Ala Tyr His Glu Ser Gly His Ala Ile Ile Ala Tyr
            595                 600                 605

Tyr Thr Lys Asp Ala Met Pro Ile Asn Lys Ala Thr Ile Met Pro Arg
        610                 615                 620

Gly Pro Thr Leu Gly His Val Ser Leu Leu Pro Glu Asn Asp Arg Trp
625                 630                 635                 640

Asn Glu Thr Arg Ala Gln Leu Leu Ala Gln Met Asp Val Ser Met Gly
                645                 650                 655

Gly Arg Val Ala Glu Glu Leu Ile Phe Gly Thr Asp His Ile Thr Thr
                660                 665                 670

Gly Ala Ser Ser Asp Phe Asp Asn Ala Thr Lys Ile Ala Lys Arg Met
            675                 680                 685

Val Thr Lys Phe Gly Met Ser Glu Lys Leu Gly Val Met Thr Tyr Ser
        690                 695                 700

Asp Thr Gly Lys Leu Ser Pro Glu Thr Gln Ser Ala Ile Glu Gln Glu
705                 710                 715                 720

Ile Arg Ile Leu Leu Arg Asp Ser Tyr Glu Arg Ala Lys His Ile Leu
                725                 730                 735

Lys Thr His Ala Lys Glu His Lys Asn Leu Ala Glu Ala Leu Leu Thr
            740                 745                 750

Tyr Glu Thr Leu Asp Ala Lys Glu Ile Gln Ile Val Leu Glu Gly Lys
        755                 760                 765

Lys Leu Glu Val Arg
    770
```

<210> SEQ ID NO 3
<211> LENGTH: 18
<212> TYPE: DNA
<213> ORGANISM: Artificial Sequence
<220> FEATURE:
<223> OTHER INFORMATION: artificially synthesized primer sequence

<400> SEQUENCE: 3
tgtaaaacga cggccagt                                             18

<210> SEQ ID NO 4
<211> LENGTH: 21
<212> TYPE: DNA
<213> ORGANISM: Artificial Sequence
<220> FEATURE:

-continued

<223> OTHER INFORMATION: artificially synthesized primer sequence

<400> SEQUENCE: 4
accatgatta cgccaagctt g                                          21

<210> SEQ ID NO 5
<211> LENGTH: 31
<212> TYPE: DNA
<213> ORGANISM: Artificial Sequence
<220> FEATURE:
<223> OTHER INFORMATION: artificially synthesized primer sequence

<400> SEQUENCE: 5
atgttttcct tgtcgagcac ggtgcaaccc c                               31

<210> SEQ ID NO 6
<211> LENGTH: 31
<212> TYPE: DNA
<213> ORGANISM: Artificial Sequence
<220> FEATURE:
<223> OTHER INFORMATION: artificially synthesized primer sequence

<400> SEQUENCE: 6
tctcggaggt agactggaga cgtcgtgtcc t                               31

<210> SEQ ID NO 7
<211> LENGTH: 499
<212> TYPE: DNA
<213> ORGANISM: Homo sapiens

<400> SEQUENCE: 7
atgttttcct tgtcgagcac ggtgcaaccc cagtttacag ttcctctgag tcatctcatc      60
aatgccttcc atacaccaaa aaacacttct gtttctctca gtggagtgtc agtttctcaa     120
aaccagcatc gagatgtagt tcctgagcat gaggctccca gcagtgagcc ttcacttaac     180
ttaagggacc ttggattatc tgaattaaaa attggacaga ttgatcagct ggtagaaaat     240
ctacttcctg gattttgtaa aggcaaaaac atttcttccc attggcatac atcccatgtc     300
tctgcacaat ccttctttga aaataaatat ggtaacttag atatatttag tacattacgt     360
tcctcttgct tgtatcgaca tcattcaaga gctcttcaaa gcatttgttc agatcttcag     420
tactggccag ttttcataca gtctcggggt tttaaaactt tgaaatcaag gacacgacgt     480
ctccagtcta cctccgaga                                                 499

<210> SEQ ID NO 8
<211> LENGTH: 166
<212> TYPE: PRT
<213> ORGANISM: Homo sapiens

<400> SEQUENCE: 8

Met Phe Ser Leu Ser Ser Thr Val Gln Pro Gln Phe Thr Val Pro Leu
 1               5                  10                  15

Ser His Leu Ile Asn Ala Phe His Thr Pro Lys Asn Thr Ser Val Ser
             20                  25                  30

Leu Ser Gly Val Ser Val Ser Gln Asn Gln His Arg Asp Val Val Pro
         35                  40                  45

Glu His Glu Ala Pro Ser Ser Glu Pro Ser Leu Asn Leu Arg Asp Leu
     50                  55                  60

Gly Leu Ser Glu Leu Lys Ile Gly Gln Ile Asp Gln Leu Val Glu Asn
 65                  70                  75                  80

```
                                -continued

Leu Leu Pro Gly Phe Cys Lys Gly Lys Asn Ile Ser Ser His Trp His
                85                  90                  95

Thr Ser His Val Ser Ala Gln Ser Phe Phe Glu Asn Lys Tyr Gly Asn
            100                 105                 110

Leu Asp Ile Phe Ser Thr Leu Arg Ser Ser Cys Leu Tyr Arg His His
        115                 120                 125

Ser Arg Ala Leu Gln Ser Ile Cys Ser Asp Leu Gln Tyr Trp Pro Val
    130                 135                 140

Phe Ile Gln Ser Arg Gly Phe Lys Thr Leu Lys Ser Arg Thr Arg Arg
145                 150                 155                 160

Leu Gln Ser Thr Ser Glu
                165

<210> SEQ ID NO 9
<211> LENGTH: 20
<212> TYPE: PRT
<213> ORGANISM: Homo sapiens
<220> FEATURE:
<223> OTHER INFORMATION: artificially synthesized peptide

<400> SEQUENCE: 9

Lys Asp Lys Ile Leu Met Gly Pro Glu Arg Arg Ser Val Glu Ile Asp
1               5                   10                  15

Asn Lys Asn Lys
            20
```